US 8,870,778 B2

(12) United States Patent
Tsutaki et al.

(10) Patent No.: US 8,870,778 B2
(45) Date of Patent: Oct. 28, 2014

(54) TRANLUMEN ENDOSCOPE INSERTION SURGERY

(75) Inventors: Shinichi Tsutaki, Hachioji (JP);
Hidemichi Aoki, Tokorozawa (JP);
Takeharu Nakazato, Koganei (JP);
Kosuke Motai, Hachioji (JP); Toshihiro Shizuka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1745 days.

(21) Appl. No.: 11/963,935

(22) Filed: Dec. 24, 2007

(65) Prior Publication Data

US 2009/0163767 A1 Jun. 25, 2009

(51) Int. Cl.
*A61B 1/018* (2006.01)
*A61B 8/00* (2006.01)
*A61B 8/14* (2006.01)
*A61B 1/273* (2006.01)
*A61B 1/04* (2006.01)
*A61B 8/12* (2006.01)

(52) U.S. Cl.
CPC ............... *A61B 1/04* (2013.01); *A61B 1/2736* (2013.01); *A61B 8/12* (2013.01)
USPC ........................... 600/462; 600/464; 600/461

(58) Field of Classification Search
None
See application file for complete search history.

(56) References Cited

U.S. PATENT DOCUMENTS

| | | | | |
|---|---|---|---|---|
| 5,054,491 A * | 10/1991 | Saito et al. | | 600/109 |
| 5,395,030 A * | 3/1995 | Kuramoto et al. | | 227/179.1 |
| 5,626,614 A | 5/1997 | Hart | | |
| 6,543,456 B1 * | 4/2003 | Freeman | | 128/898 |
| 7,654,951 B2 * | 2/2010 | Ishikawa | | 600/114 |
| 2004/0186514 A1 * | 9/2004 | Swain et al. | | 606/224 |
| 2004/0225191 A1 * | 11/2004 | Sekine et al. | | 600/178 |
| 2005/0256402 A1 * | 11/2005 | Kawashima et al. | | 600/437 |
| 2006/0206063 A1 * | 9/2006 | Kagan et al. | | 604/264 |
| 2006/0229643 A1 * | 10/2006 | Nolan et al. | | 606/153 |
| 2007/0232922 A1 * | 10/2007 | Kohno | | 600/459 |

FOREIGN PATENT DOCUMENTS

JP 2004-267772 9/2004

* cited by examiner

*Primary Examiner* — Michael Rozanski
*Assistant Examiner* — Lawrence Laryea
(74) *Attorney, Agent, or Firm* — Scully, Scott, Murphy & Presser, P.C.

(57) ABSTRACT

An intraluminal endoscope inserting method according to the present invention is a method of forming a first opening in a wall of a first luminal organ while observing optical and ultrasonic images formed by an ultrasonic endoscope inserted into a first luminal organ through a natural opening, forming a second opening in a wall of a desired second luminal organ adjacent to the first luminal organ through an abdominal cavity space from the first opening, leading the ultrasonic endoscope into a second luminal organ from a second opening and performing observation and treatment, and after the treatment and the like, stitching the openings. This makes it possible to insert the endoscope with a skill same as that required for a normal endoscope test and makes it easy to insert the endoscope even into luminal organs irregularly connected to with one another in a body cavity.

20 Claims, 21 Drawing Sheets

TRANLUMEN ENDOSCOPE INSERTION SURGERY

BACKGROUND OF THE INVENTION

1. Field of the Invention

The present invention relates to an intraluminal endoscope inserting method for an endoscope, and, more particularly to an intraluminal endoscope inserting method for an endoscope into luminal organs irregularly arranged in a body cavity.

2. Description of the Related Art

In recent years, researches concerning surgery called NOTES™ surgery (Natural Orifice Translumenal Endoscopic Surgery) for forming, while observing an image formed by an endoscope led into a luminal organ through a natural opening, an opening on a wall surface of the luminal organ, leading the endoscope into an abdominal cavity from the opening, and performing observation and treatment for intra-abdominal organs have been actively performed. Various proposals concerning endoscopes and treatment instrument systems used for the surgery have been made by, for example, Japanese Patent Laid-Open No. 2004-267772.

On the other hand, it is disclosed that an opening or the like is temporarily held by using a T-bar unit such as "T-ANCHOR SUTURING DEVICE" described in, for example, U.S. Pat. No. 5,626,614 and a technique for making it possible to efficiently carrying out manipulation has been developed.

In particular, in advanced countries, various diseases due to obesity pose a problem. For example, patients (including potential patients) in an obesity state with, for example, BMI exceeding 30 are increasing. Measures for such patients in the obesity state are developed into a social problem. As a solution against the problem, weight loss treatments are applied to the patients in the obesity state. In general, as the weight loss treatments, medical treatments as combinations of diet instructions, physical exercise instructions, and the like are carried out under weight loss monitoring and observation in medical facilities and the like.

However, in the medical weight loss treatments, cooperation of the patients in the obesity state is indispensable. A resultant increase in various diseases due to obesity indicates that a sufficient effect cannot always be obtained under the present situation.

Therefore, in recent years, in particular, in the United States and the like, an inter-digestive tract bypass surgery for physically suppressing, by bypassing the digestive tracts using a so-called Roux-en-Y method used in gastric resection or the like, a digestive action for foods in digestive tracts regardless of an intention of a patient to effectively prevent nutrition ingestion and perform anti-obesity measures has been performed.

In such an inter-digestive tract bypass surgery, for example, the jejunum is caused to play a role of bypass and the duodenum is necessary as a digestive tract in order to secure various kinds of external secretion and the like. Therefore, the distal end of the jejunum is connected to an upper part of the stomach and bypassed to the small intestine and the duodenum is Y-connected to the proximal end of the jejunum to secure internal secretion and a digestive enzyme such as pancreatic juice.

Therefore, since a state in the body cavity, luminal organs are irregularly arranged, i.e., (a part of) the stomach is held as the remaining stomach, and digestion in the stomach is impossible. Consequently, surgical weight loss treatment can be attained by the inter-digestive tract bypass surgery.

There is a problem in that, for such a patient, it is difficult to insert the endoscope and, even if it is possible to insert the endoscope, treatment is difficult and endoscope test/treatment is difficult.

SUMMARY OF THE INVENTION

An intraluminal endoscope inserting method according to claim 1 of the present invention includes:

an endoscope inserting step of inserting an insertion portion of an endoscope into a first object luminal organ through a natural opening of a patient whose luminal organs are irregularly connected to one another in a body cavity;

a first opening forming step of forming a first opening in a tube wall of the first object luminal organ;

a second opening forming step of forming a second opening in a tube wall of the second object luminal organ;

an object organ entering step of causing a distal end of the insertion section of the endoscope to enter an internal area of the second object luminal organ from the second opening; and an observing and treating step of observing and treating the second object luminal organ with the endoscope.

Other characteristics and advantages of the present invention will be sufficiently made apparent by the following explanation.

BRIEF DESCRIPTION OF THE DRAWINGS

FIG. 1 is a schematic diagram showing the entire structure of an ultrasonic endoscope system.

FIG. 2 is an external view showing the structure of a distal end of the ultrasonic endoscope shown in FIG. 1.

FIG. 3 is a diagram showing the structure of a T-bar portion of a T-bar unit inserted into the ultrasonic endoscope shown in FIG. 1 to be used.

FIG. 4 is a diagram showing the structure of a T-bar injection portion of the T-bar unit inserted through the ultrasonic endoscope shown in FIG. 1 to be used.

FIG. 5 is a diagram showing the structure of a modification of the T-bar portion of the T-bar unit shown in FIG. 3.

FIG. 6 is a diagram showing the structure of a multi-lumen tube through which the ultrasonic endoscope shown in FIG. 1 is inserted.

FIG. 7 is a sectional view showing a section taken along line A-A shown in FIG. 6.

FIG. 8 is an overall diagram showing a system configuration for explaining actions of the ultrasonic endoscope system.

FIG. 9 is a first diagram for explaining an example of an arrangement of luminal organs to which an intraluminal endoscope inserting method by the ultrasonic endoscope system shown in FIG. 8 is applied.

FIG. 10 is a second diagram for explaining an example of an arrangement of luminal organs to which the intraluminal endoscope inserting method by the ultrasonic endoscope system shown in FIG. 8 is applied.

FIG. 11 is a third diagram for explaining an example of an arrangement of luminal organs to which the intraluminal endoscope inserting method by the ultrasonic endoscope system shown in FIG. 8 is applied.

FIG. 12 is a fourth diagram for explaining an example of an arrangement of luminal organs to which the intraluminal endoscope inserting method by the ultrasonic endoscope system shown in FIG. 8 is applied.

FIG. 13 is a fifth diagram for explaining an example of an arrangement of luminal organs to which the intraluminal endoscope inserting method by the ultrasonic endoscope system shown in FIG. 8 is applied.

FIG. 14 is a diagram showing a modification of an insertion path shown in FIG. 13.

FIG. 15 is a first flowchart for explaining a flow of the intraluminal endoscope inserting method by the ultrasonic endoscope system shown in FIG. 8.

FIG. 16 is a second flowchart for explaining a flow of the intraluminal endoscope inserting method by the ultrasonic endoscope system shown in FIG. 8.

FIG. 17 is a first diagram for explaining the flowcharts shown in FIGS. 15 and 16.

FIG. 18 is a second diagram for explaining the flowcharts shown in FIGS. 15 and 16.

FIG. 19 is a third diagram for explaining the flowcharts shown in FIGS. 15 and 16.

FIG. 20 is a fourth diagram for explaining the flowcharts shown in FIGS. 15 and 16.

FIG. 21 is a fifth diagram for explaining the flowcharts shown in FIGS. 15 and 16.

FIG. 22 is a sixth diagram for explaining the flowcharts shown in FIGS. 15 and 16.

FIG. 23 is a seventh diagram for explaining the flowcharts shown in FIGS. 15 and 16.

FIG. 24 is an eighth diagram for explaining the flowcharts shown in FIGS. 15 and 16.

FIG. 25 is a ninth diagram for explaining the flowcharts shown in FIGS. 15 and 16.

FIG. 26 is a tenth diagram for explaining the flowcharts shown in FIGS. 15 and 16.

FIG. 27 is an eleventh diagram for explaining the flowcharts shown in FIGS. 15 and 16.

FIG. 28 is a twelfth diagram for explaining the flowcharts shown in FIGS. 15 and 16.

FIG. 29 is a first diagram for explaining actions of the modification in the flowcharts shown in FIGS. 15 and 16.

FIG. 30 is a second diagram for explaining actions of the modification in the flowcharts shown in FIGS. 15 and 16.

FIG. 31 is a third diagram for explaining actions of the modification in the flowcharts shown in FIGS. 15 and 16.

FIG. 32 is a fourth diagram for explaining actions of the modification in the flowcharts shown in FIGS. 15 and 16.

FIG. 33 is a fifth diagram for explaining actions of the modification in the flowcharts shown in FIGS. 15 and 16.

FIG. 34 is a sixth diagram for explaining actions of the modification in the flowcharts shown in FIGS. 15 and 16.

DETAILED DESCRIPTION OF THE PREFERRED EMBODIMENTS

The present invention will be hereinafter explained with reference to embodiments shown in the figures.

First Embodiment

Figure 1:
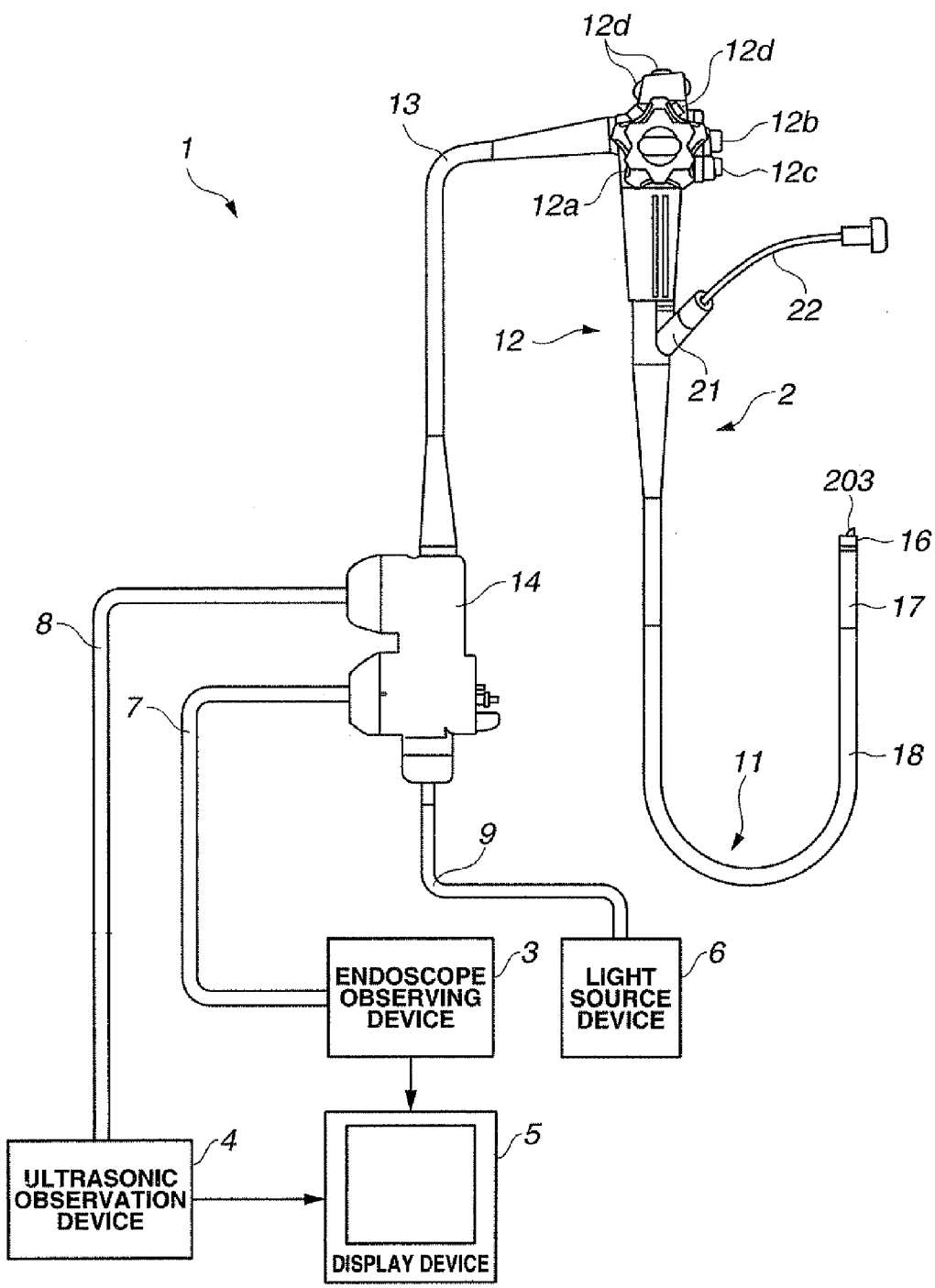
FIGS. 1 to 7 relate to a first embodiment of the present invention.

As shown in FIG. 1, an ultrasonic endoscope system 1 according to a first embodiment of the present invention mainly includes an ultrasonic endoscope 2 that includes an endoscope observing unit (not shown) having an endoscope observing function and an ultrasonic observation unit (not shown) having an ultrasonic observation function, an endoscope observing device 3 that processes control of the endoscope observing unit and an output signal thereof, an ultrasonic observation device 4 that processes control of the ultrasonic observation unit and an output signal thereof, a display device 5 that receives the respective signals from the endoscope observing device 3 and the ultrasonic observation device 4 and appropriately displays an endoscope image and an ultrasonic tomographic image, a light source device 6 that is a light source of illumination light emitted from a front surface of a distal end of the endoscope observing unit, a video cable 7, an ultrasonic cable 8, and a light source cable 9.

Figure 2:
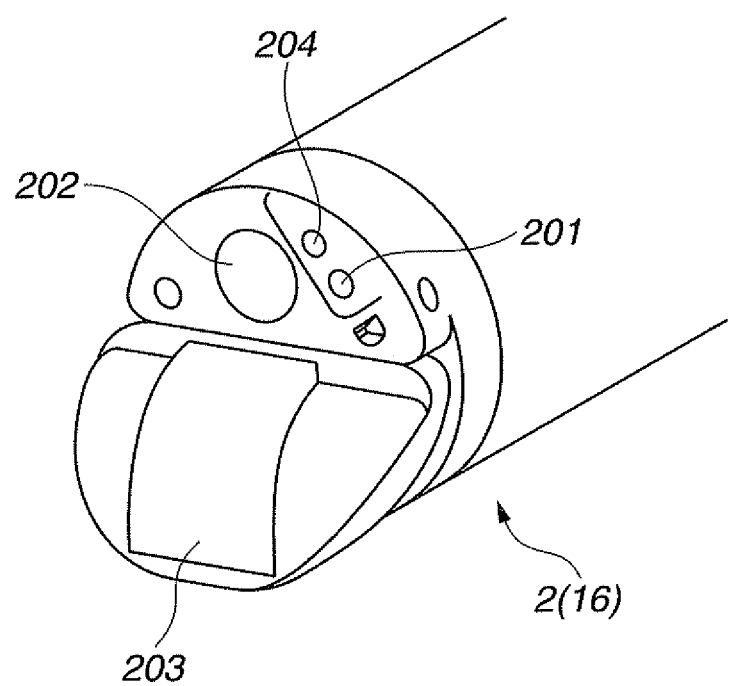

The ultrasonic endoscope 2 in the ultrasonic endoscope system 1 is, as shown in FIG. 2, a convex-type ultrasonic endoscope that includes an ultrasonic transducer for scanning, for example, a surface parallel to a front side of an ultrasound insertion axis. A direct-vision convex-type ultrasonic endoscope device or the like is applied as the ultrasonic endoscope 2. In the direct-view convex-type ultrasonic endoscope device, a treatment instrument channel is arranged such that, on a distal end surface, an observation direction of an observation window 201 for guiding an observation image to an image pickup device (not shown) in the distal end and a direction in which a distal end opening 202 of a treatment instrument channel 11a (see FIG. 6) faces are substantially parallel to an endoscope insertion axis.

On the distal end surface of the ultrasonic endoscope 2, an illumination window 202 for emitting illumination light from the light source device 6 is provided adjacent to the observation window 201. The illumination light emitted from the illumination window 204 is transmitted through an optical fiber bundle (not shown) through which an insertion portion 11 is inserted from the light source device 6.

Referring back to FIG. 1, the ultrasonic endoscope 2 mainly includes a slim insertion portion 11 inserted into a body cavity, an operation portion 12 continuously provided on a proximal end side of the insertion portion 11 and used for operating the insertion portion 11, a universal cable 13 extending from a side of the operation portion 12, and a connector portion 14 provided at one end of the universal cable 13.

The insertion portion 11 mainly includes, in order from a distal end side thereof, a distal end rigid portion formed of a rigid member, a bending portion 17 continuously provided on a proximal end side of the distal end rigid portion 16 and formed to freely bend, and a flexible tube portion 18, one end of which is continuously provided on a proximal end side of the bending portion 17 and the other end of which is continuously provided on a distal end side of the operation portion 12, and that is formed in a thin and long shape with flexibility. In the insertion portion 11, a treatment instrument channel (not specifically shown in the figure) inserted through between the proximal end and the distal end thereof is formed.

In the inside of the distal end side of the distal end rigid portion 16, although not shown in the figure, an endoscope observing unit and an ultrasonic observation unit are disposed. In the ultrasonic observation unit, plural ultrasonic transducers that transmit and receive ultrasounds are arrayed to form an ultrasound scanning surface. The ultrasonic observation unit can acquire an ultrasonic signal that contributes to creation of a tomographic image further in the inside than a body cavity wall (an ultrasonic tomographic image). The endoscope observing unit has an observation optical member, an illumination optical member, an image pickup device, and the like. The endoscope observing unit can obtain an image pickup signal that contributes to generation of an image signal for optically picking up an image of the surface of the body cavity wall and displaying an endoscope image for observation.

The operation unit 12 includes operation members for performing various kinds of operation of the ultrasonic endoscope 2 such as an angle knob 12a that is an operation member for carrying out bending operation on the bending portion 17 of the insertion portion 11 in the four directions freely, a suction button 12b for performing suction operation, an air-supply and water-supply button 12c for performing air supply and water supply operation, and plural operation members 12d for performing various kinds of operation such as display switching for the display device 5 and freeze instruction and release instruction for a display image.

Further, in the operation unit 12, a treatment instrument insertion opening 21 serving as an insertion opening for inserting, in using the ultrasonic endoscope 2, the ultrasonic endoscope 2 through a treatment instrument channel (not shown) in the insertion portion 11 and leading various treatment instruments 22 into the body cavity is provided near the distal end side in a state protruding from the operation unit 12.

The universal cable 13 is a cable that is disposed to extend from the side of the operation unit 12 as described above and through which various plural signal lines and the like for transmitting electric signals and the like and an optical fiber cable and the like for illumination line are inserted therein. A connector portion 14 for securing connection of the respective devices of the endoscope observing device 3, the ultrasonic observation device 4, and the light source device 6 for the ultrasonic endoscope 2 are disposed at a distal end portion of the universal cable 13.

The endoscope observing device 3 is an optical image processing device that controls to drive the image pickup device of the endoscope observing unit of the ultrasonic endoscope 2 to receive an image pickup signal transmitted from the image pickup device, perform various kinds of signal processing, and generate a video signal for an endoscope optical observation image.

The ultrasonic observation device 4 is an ultrasonic image processing device that controls to drive an ultrasonic transducer of an ultrasonic transducer unit 203 of the ultrasonic endoscope 2 to transmit ultrasound of a predetermined frequency to an observation object and receive, from the ultrasonic transducer, an electric signal obtained by receiving the ultrasound reflected by the observation object. The ultrasonic observation device 4 performs various kinds of signal processing to generate a video signal for an ultrasonic tomographic image.

The display device 5 is a device that receives the various video signals generated by the ultrasonic observation device 4 and the endoscope observing device 3 to display observation images corresponding to the video signals, respectively, i.e., the ultrasonic tomographic image and the optical observation image by appropriately switching the images or simultaneously display the images.

The light source device 6 is a device that supplies illumination light for illuminating the front of the ultrasonic endoscope 2 through an illumination window 204 provided on a front portion at the distal end of the endoscope observing unit of the ultrasonic endoscope 2.

The ultrasonic cable 8 is a connection cable that electrically connects the ultrasonic observation device 4 and the ultrasonic endoscope 2.

The video cable 7 is a connection cable that electrically connects the endoscope observing device 3 and the ultrasonic endoscope 2.

The light source cable 9 is an optical fiber cable made of an optical fiber bundle that connects the light source device 6 and the ultrasonic endoscope 2, and guides the illumination light from the light source device 6 to the illumination window 204 of the endoscope observing unit in the ultrasonic endoscope 2.

The treatment instrument insertion opening 21 provided in the operation unit 12 of the ultrasonic endoscope 2 connects to a treatment instrument channel 11a (see FIG. 6) formed to be inserted through to the distal end opening 202 (see FIG. 2) provided on the front side of the distal end rigid portion 16 from the inside of the operation unit 12 via the inside of the insertion portion 11. Therefore, the various treatment instruments 22 inserted from the treatment instrument insertion opening 21 can be inserted through the treatment instrument channel 11a, and pushed out from and pulled into the distal end opening 202 of the insertion portion 11.

A rising stand (not shown) for operating the treatment instruments and the like may be provided at the distal end opening 202 of the treatment instrument channel 11a.

Examples of the treatment instruments 22 inserted from the treatment instrument insertion opening 21 include an electric cautery as an opening forming treatment instrument that is an opening treatment instrument for an endoscope that dissections a desired region of the luminal organs and forms an opening under observation by the ultrasonic endoscope 2, a balloon treatment instrument as an expansion treatment instrument for expanding spaces among the luminal organs before forming the opening, a T-bar unit as a holding treatment instrument that perform treatment for holding an opening state of the opening, a treatment instrument that treats the pancreatic duct and the biliary, and a diagnostic device that makes a diagnosis of the pancreatic duct and the biliary.

The surgical treatment instrument 22 for performing a surgical operation of the intra-abdominal organs under the observation by the ultrasonic endoscope 2, and a suture instrument for suturing the opening opened under the observation by the ultrasonic endoscope 2 are inserted into the treatment instrument channel 11a of the treatment instrument insertion opening 21. This makes it possible to perform various kinds of treatment such as the surgical operation of the intra-abdominal organs under the observation by the ultrasonic endoscope 2.

Figure 3:
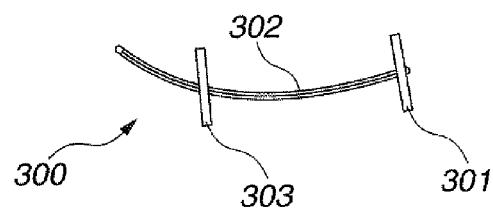
Figure 4:
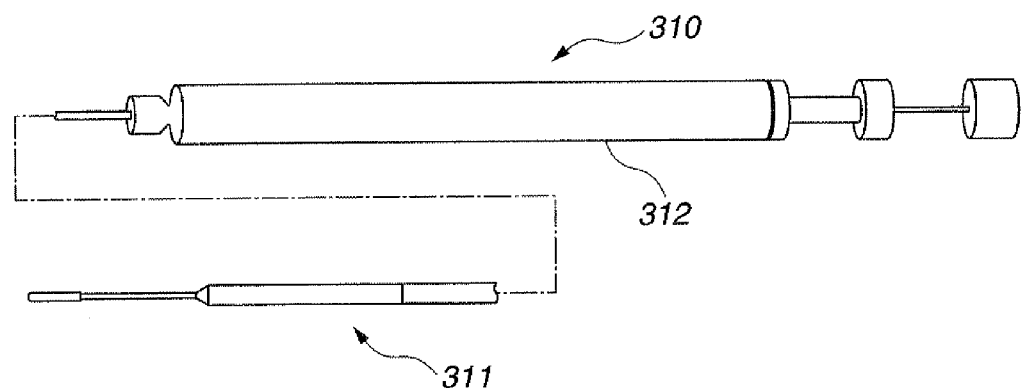

The T-bar unit includes a T-bar portion 300 shown in FIG. 3 and a T-bar injection portion 310 shown in FIG. 4. The T-bar portion 300 includes a bar-like distal end bar member 301, a thread-like member 302 that is connected to the center of the distal end bar member 301 and has the distal end bar member 301 at the distal end thereof, and a center bar member 303, to the center of which the thread-like member 302 is connected. By moving the center bar member 303 along the thread-like member 302, it is possible to hold an organism tissue with the distal end bar member 301 and the center bar member 303 (see FIG. 3). The T-bar injection portion 310 includes a needle-like member 311 through which the T-bar portion 300 is inserted and a T-bar push-out portion 312 that pushes out the T-bar portion 300 in the needle-like member 311 to a distal end side of the needle-like member 311. The needle-like member 311 can be inserted through the treatment instrument channel 11a (see FIG. 4).

Figure 5:
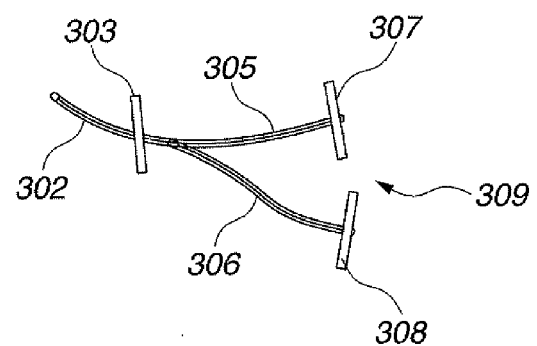

As a modification of the T-bar portion 300, as shown in FIG. 5, it is also possible to use a forked T-bar portion 309 including a first thread-like member 305 and a second thread-like member 306, which is obtained by dividing the thread-like member 302 into two at a distal end side thereof from the center bar member 303, and a first distal end bar member 307 and a second distal end bar member 308 provided on distal end sides of the first thread-like member 305 and the second thread-like member 306, respectively.

Figure 6:
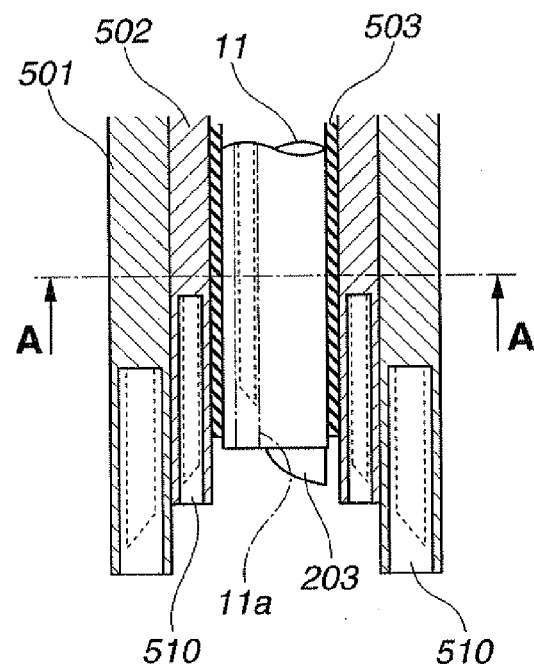
Figure 7:
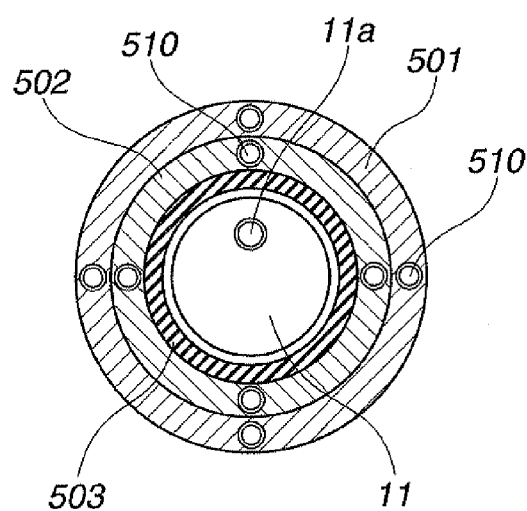

The ultrasonic endoscope 2 is provided with the insertion portion 11 in a multi-lumen tube 500 formed of plural cylindrical members of a laminated wall structure that includes plural channels 510 for inserting the various treatment instruments as shown in FIGS. 6 and 7.

The multi-lumen tube 500 is formed in, for example, a three-layer structure including three layers of cylindrical members. The plural channels 510 for inserting the plural various treatment instruments are formed in walls of a cylindrical member 501 in an outermost layer and a cylindrical member 502 in an intermediate layer, respectively. The insertion portion 11 of the ultrasonic endoscope 2 is inserted through a cylindrical member 503 in an innermost layer of the multi-lumen tube 500. The cylindrical members 501 to 503 can hold the members inserted therethrough (the cylindrical member 502 is inserted through the cylindrical member 501, the cylindrical member 503 is inserted through the cylindrical member 502, and the insertion portion 11 of the ultrasonic endoscope 2 is inserted through the cylindrical member 503) to freely move forward and backward.

Manipulation performed by using the ultrasonic endoscope system 1 according to the present embodiment is explained below with reference to FIGS. 8 to 28. FIGS. 8 to 28 are diagrams for explaining a procedure and the like of the manipulation and schematically show, for example, an arrangement relation of various organs and the like in the body cavity.

Endoscope manipulation performed by using the ultrasonic endoscope system 1 according to the present embodiment explained below is an intraluminal endoscope inserting method for observing and treating luminal organs of, for example, a patient (e.g., a patient to whom an inter-digestive tract bypass surgery for surgical treatment as anti-obesity measures is applied), whose luminal organs are irregularly connected to one another in the body cavity.

In the intraluminal endoscope inserting method, roughly, first, a surgeon forms a first opening in a wall of a first luminal organ while observing optical and ultrasonic images formed by the ultrasonic endoscope 2 inserted into the first luminal organ through a natural opening. Next, the surgeon forms a second opening in a wall of a desired second luminal organ adjacent to the first luminal organ through an abdominal cavity space from the first opening. Moreover, the surgeon leads the ultrasonic endoscope 2 into the second luminal organ from the second opening and performs observation and treatment. After the treatment and the like, the surgeon stitches the openings.

Figure 8:
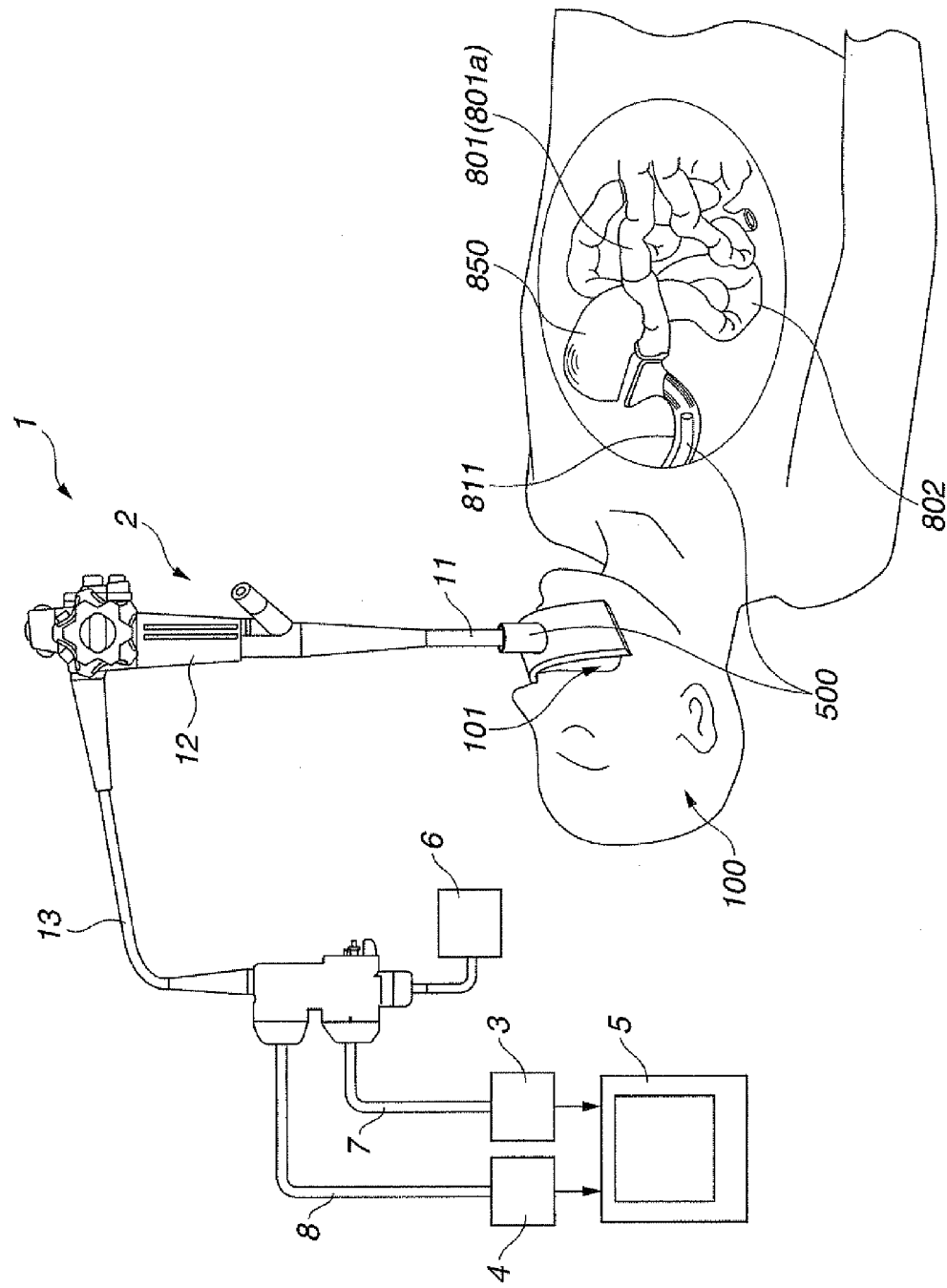
FIGS. 8 to 14 relate to the first embodiment of the present invention.

First, in FIG. 8, the surgeon energizes the various devices in the ultrasonic endoscope system 1 to make the system operational.

In the state, the surgeon inserts the insertion portion 11 of the ultrasonic endoscope 2 up to, for example, an inside of a distal end portion of the esophagus, which is a first object luminal organ, in a tube wall of which an opening is formed, from a natural opening, for example, a mouth cavity 101 of a patient 100 or the like while observing an endoscope image displayed on the display device 5. Here, the first object luminal organ refers to an organ into which the ultrasonic endoscope can be inserted from the natural opening in a normal procedure. Operation for inserting the ultrasonic endoscope 2 in the case is the same operation as that of a flexible endoscope test carried out in general. The insertion portion 11 of the ultrasonic endoscope 2 is inserted through the multi-lumen tube 500.

The luminal organs are irregularly connected to one another in the body cavity of the patient, who is a subject of the intraluminal endoscope inserting method are explained.

Figure 9:
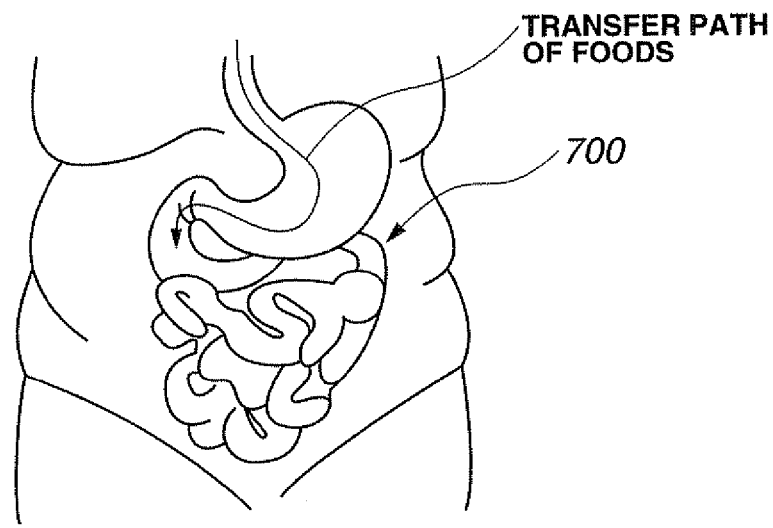

In general, luminal organs 700 of a healthy person are arranged in a connected structure as shown in FIG. 9. The insertion portion 11 of the ultrasonic endoscope 2 can reach a desired luminal organ through the same course as a transfer path of foods.

Figure 10:
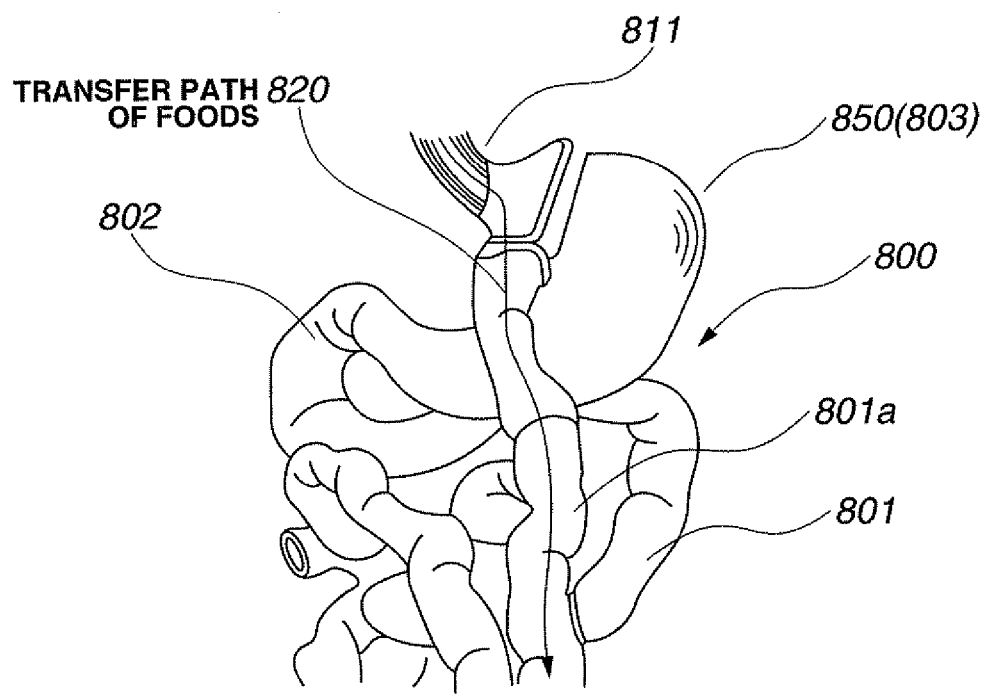

However, in luminal organs 800 of a patient subjected to the inter-digestive tract bypass surgery by the Roux-en-Y method or the like for, for example, obesity treatment, as shown in FIG. 10, a jejunum 801 is caused to play a role of a bypass (since a duodenum 802 is necessary as a digestive tract in order to secure various kinds of external secretion and the like, a distal end of the jejunum 801 is connected to an upper part of a stomach 803 or a periphery portion of an esophagus 811 and a bypass jejunum portion 801a is Y-connected to the jejunum 801 to bypass the luminal organ 800). The stomach (a part of the stomach) 803 remains as a remaining stomach 850, which is not present in a course of the transfer path of foods 820. Therefore, a connection structure of the luminal organs 800 is extremely different from the luminal organs 700 (see FIG. 9) of the healthy person.

Figure 11:
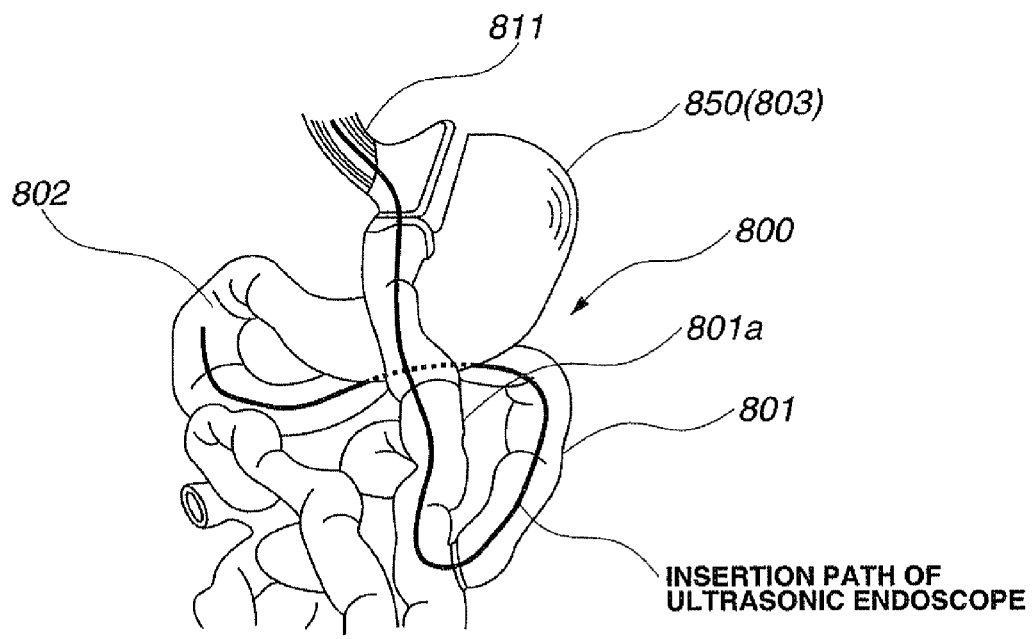

When the duodenum 802 of the patient, whose luminal organs are irregularly connected to one another in the body cavity, with the ultrasonic endoscope 2, in the past, as shown in FIG. 11, it is necessary to insert the ultrasonic endoscope 2 through a path of the esophagus 811, the bypass jejunum portion 801a, a Y connection portion 810, and the duodenum 802. However, such a path is extremely different from an insertion path of an endoscope inserting method applied to a normal healthy person. Therefore, the manipulation is extremely difficult (in particular, for a surgeon inexperienced in insertion manipulation).

Figure 12:
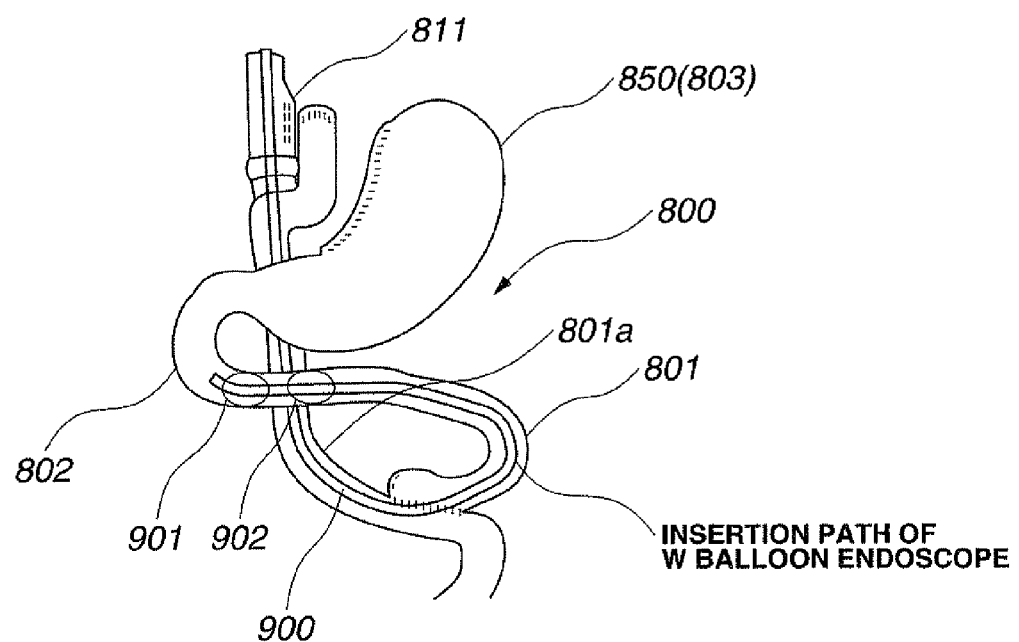

In order to solve such a problem, for example, it is possible to use a publicly-known W balloon endoscope 900 that includes, as shown in FIG. 12, two balloons 901 and 902 at a distal end thereof, deflates and inflates these balloons 901 and 902 to pull the jejunum 801 and the duodenum 802 and move the insertion portion forward and backward in the luminal organs. However, there is still a problem in that, for example, insertion takes time.

When the jejunum 801 and the duodenum 802 adhere to peripheral tissues because of a surgical operation, the W balloon endoscope 900 may not be able to be inserted into the jejunum 801 and the duodenum 802. Since the W balloon endoscope 900 is a direct-vision endoscope, in treatment, it is difficult to perform treatment for the biliary and the pancreas, which are present on the wall surface of the duodenum 802, through a nipple.

Figure 13:
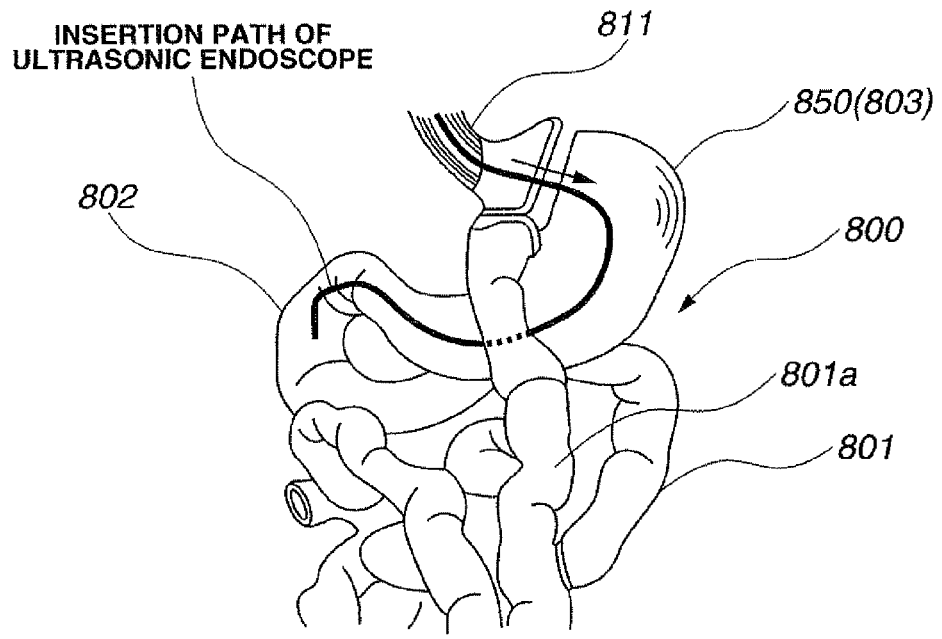

It is an object of the present embodiment to make it possible to, as shown in FIG. 13, insert the insertion portion 11 to the remaining stomach 850, and by inserting the insertion portion 11 through a path of the esophagus 811, (the bypass jejunum portion 801a), the remaining stomach 850, and the duodenum 802, make it possible to set an endoscope inserting step substantially identical with an endoscope inserting step for a healthy person, make it possible to insert the endoscope with the same skill as that required for a normal endoscope test, and make it easy to insert the endoscope even to the luminal organs irregularly connected to one another in the body cavity.

Figure 14:
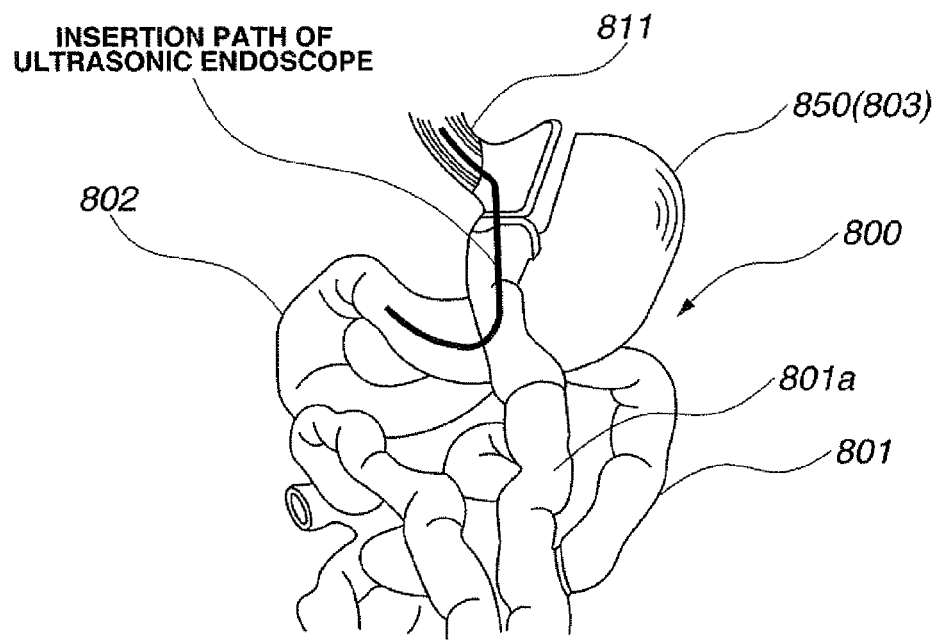

As shown in FIG. 14, in order to observe the remaining stomach 850, by inserting the insertion portion 11 through a path of the esophagus 811, the bypass jejunum portion 801a, and the remaining stomach 850, it is possible to easily insert the endoscope even to the luminal organs irregularly connected to one another in the body cavity.

Figure 15:
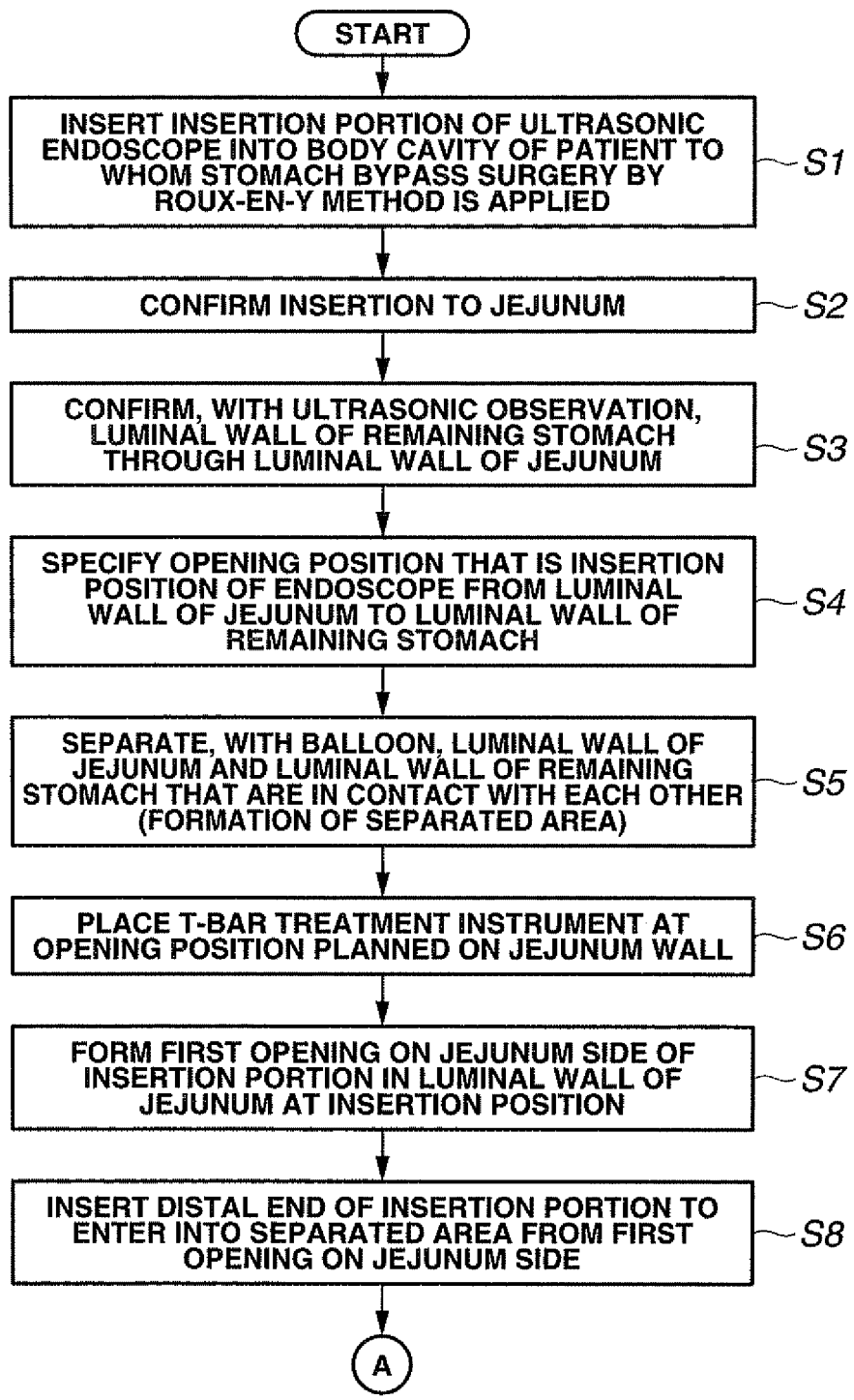
FIGS. 15 to 28 relate to the first embodiment of the present invention.
Figure 16:
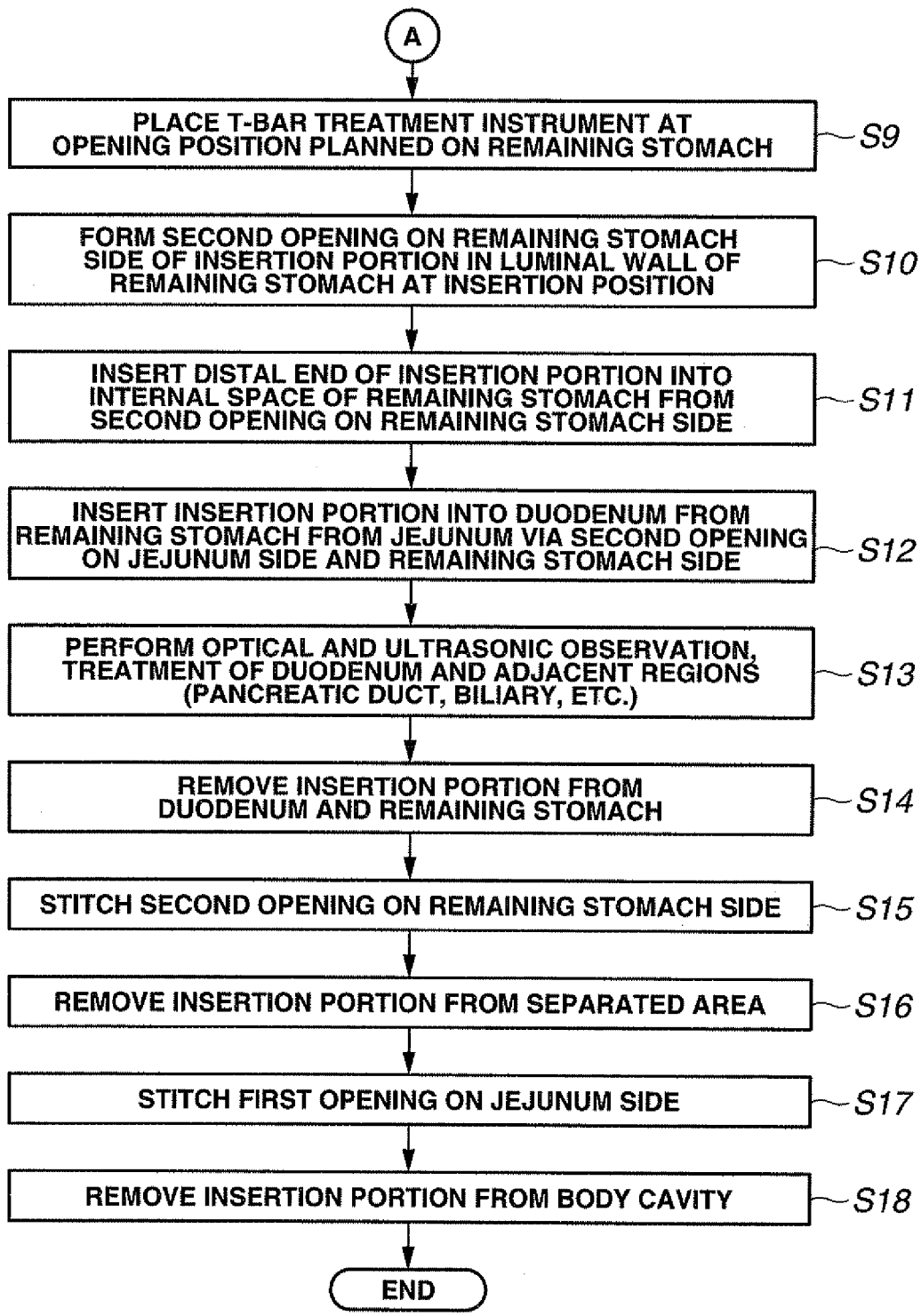

As shown in FIGS. 15 and 16, the ultrasonic endoscope system 1 starts, as the endoscope inserting step, in step S1, insertion of the insertion portion 11 of the ultrasonic endoscope 2 into the natural opening, for example, the mouth cavity 101 of a patient 100 or the like in the intraluminal endoscope inserting method for the patient 100 to whom an inter-digestive tract bypass surgery for surgical treatment as anti-obesity measures is applied by, for example, the Roux-en-Y method (see FIG. 8). In step S2, the ultrasonic endoscope system 1 checks, with optical observation of the ultrasonic endoscope 2, insertion of the insertion portion 11 into the jejunum 801, which is a first object luminal organ in which an opening is formed in a tube wall thereof, from the esophagus 811.

Figure 17:
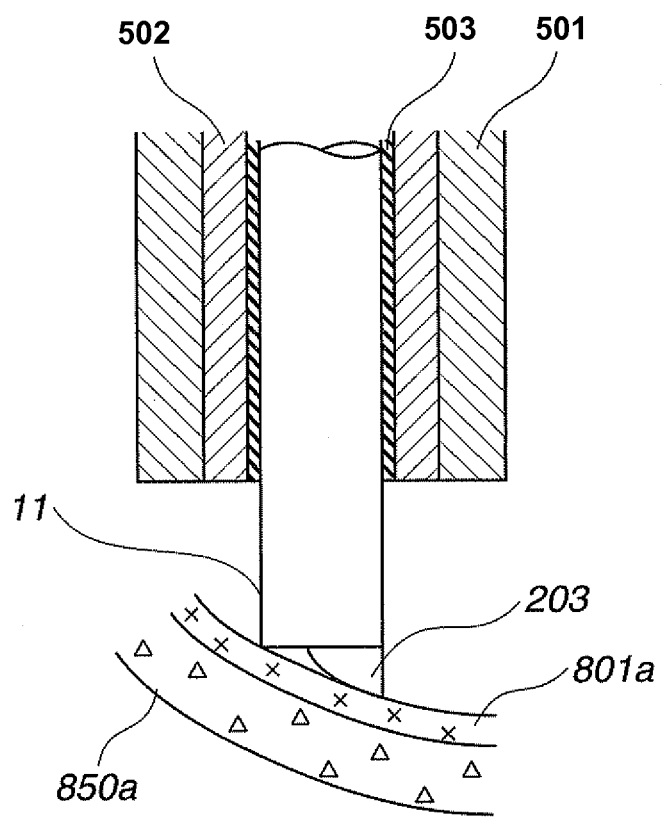

Next, as shown in FIG. 17, as an adjacent organ confirming step, in step S3, the ultrasonic endoscope system 1 protrudes the insertion portion 11 of the ultrasonic endoscope 2 from the multi-lumen tube 500 and brings the ultrasonic transducer unit 203 of the ultrasonic endoscope 2 into contact with an inner wall surface on a proximal end side (the esophagus 811 side) of the jejunum 801. The ultrasonic endoscope system 1 transmits/receives ultrasound using the ultrasonic transducer unit 203 and confirms, with ultrasonic observation, that a luminal wall 850a of the remaining stomach 850, which, for example, circumscribes the outside of a luminal wall 801b of the jejunum 801, is present.

Moreover, as a safe area confirming step, in step S4, the ultrasonic endoscope system 1 confirms, with ultrasonic observation, that other luminal organs (including blood vessels) are not present between the luminal wall 801b of the jejunum 801 and the luminal wall 850a of the remaining stomach 850.

Figure 18:
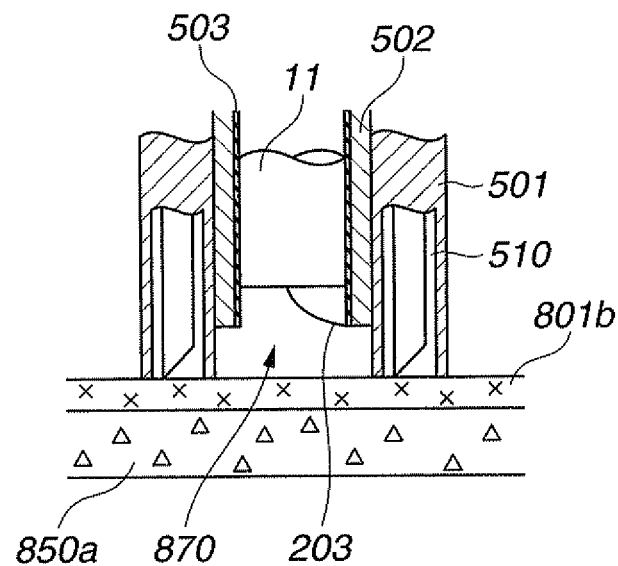
Figure 19:
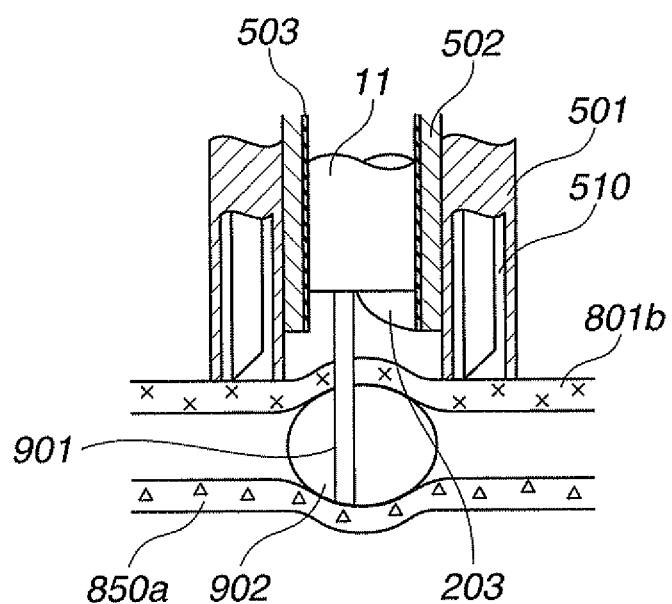

As a separated area formation step, in step S5, as shown in FIG. 18, the ultrasonic endoscope system 1 locates the multi-lumen tube 500 in front of the insertion portion 11 and brings at least a distal end of the cylindrical member 501 in the outermost circumference of the multi-lumen tube 500 into contact with an inner wall of the luminal wall 801b. In the state, as shown in FIG. 19, the ultrasonic endoscope system 1 punctures a distal end of the balloon treatment instrument 901 between the luminal wall 801b of the jejunum 801 and the luminal wall 850a of the remaining stomach 850 in a specified opening position of the insertion portion 11 from the distal end opening 202 of the treatment instrument channel 11a. The ultrasonic endoscope system 1 inflates the balloon 902 at the distal end of the balloon treatment instrument 901 to separate the luminal wall 801b of the jejunum 801 and the luminal wall 850a of the remaining stomach 850.

Water may be filled in a space 870 surrounded by an distal end surface of the insertion portion 11, an inner surface of the luminal wall 801b of the jejunum 801, and an inner surface of the multi-lumen tube 500 shown in FIG. 18 to draw an ultrasonic image or the ultrasonic endoscope may be brought into contact with wall surfaces to perform a surgical operation under ultrasonic guide.

The balloon treatment instrument 901 may include a Veress needle mechanism to prevent a blade tip from being pulled into a needle tube and scratching the luminal wall 850a when the balloon treatment instrument 901 punctures through the luminal wall 801b.

Figure 20:
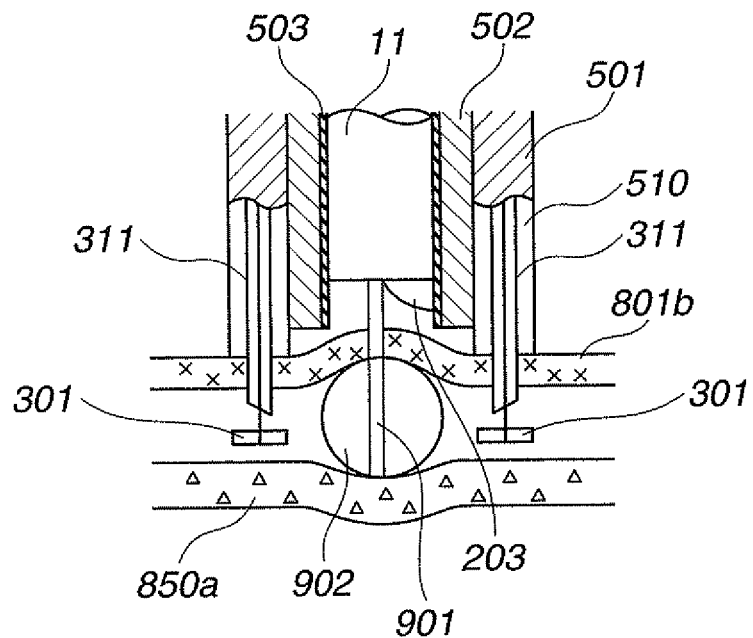
Figure 21:
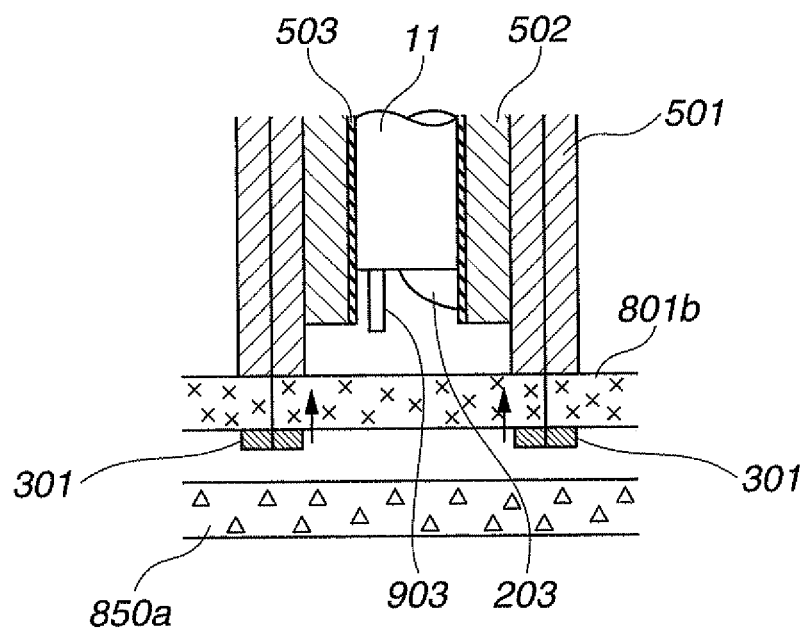

Next, as a first position holding step, in step S6, as shown in FIG. 20, the ultrasonic endoscope system 1 inserts the needle-like member 311 of the T-bar injection portion 310 to the channel 510 of the cylindrical member 501 in an outermost circumference of the multi-lumen tube 500. The ultrasonic endoscope system 1 pushed out a distal end of the needle-like member 311 from the channel 510, punctures the distal end between the luminal wall 801b of the jejunum 801 and the luminal wall 850a of the remaining stomach 850 separated from each other, and locates the distal end bar member 301 of the T-bar portion 300 between the luminal wall 801b of the jejunum 801 and the luminal wall 850a of the remaining stomach 850 from the distal end of the needle-like member 311. Subsequently, as shown in FIG. 21, the ultrasonic endoscope system 1 pulls the thread-like member 302 of the T-bar portion 300 to the proximal end side of the insertion portion 11 to hold the distal end of the cylindrical member 501 in the outermost circumference of the multi-lumen tube 500 in a state in which the distal end is in contact with the inner wall of the luminal wall 801b of the jejunum 801. Consequently, a position of the distal end of the insertion portion 11 is held in a portion where the first opening is formed.

To separate the luminal wall 801b and the luminal wall 850a, without using a balloon, it is also possible that the luminal wall 801a is sucked to be closely attached to the three-layer tube, and the tube is pulled back to the opening side to separate both the walls (the luminal wall 801b and the luminal wall 850a) from each other. Alternatively, it is also possible that a puncture needle is located to place a needle tip between both the walls (the luminal wall 801b and the luminal wall 850a) and CO2 is supplied to separate both the walls from each other.

Figure 22:
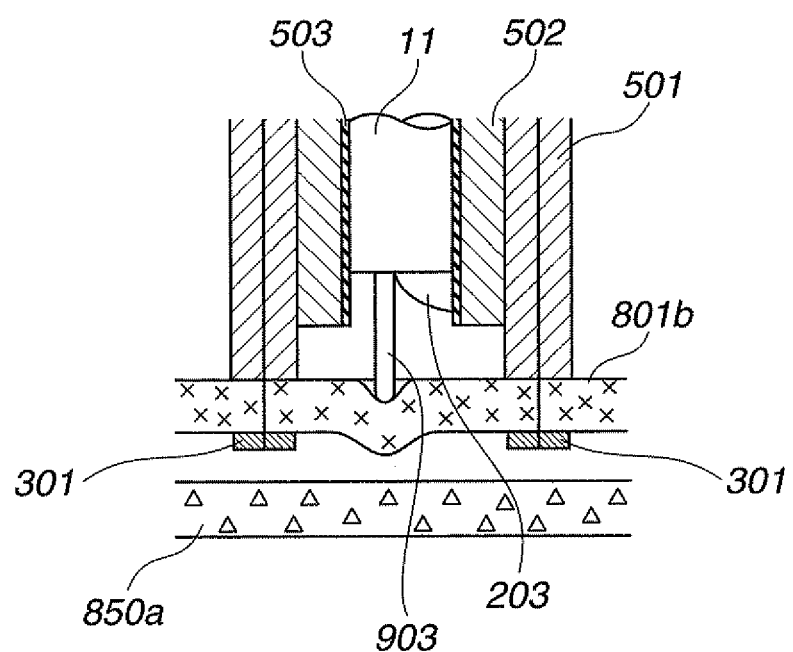
Figure 23:
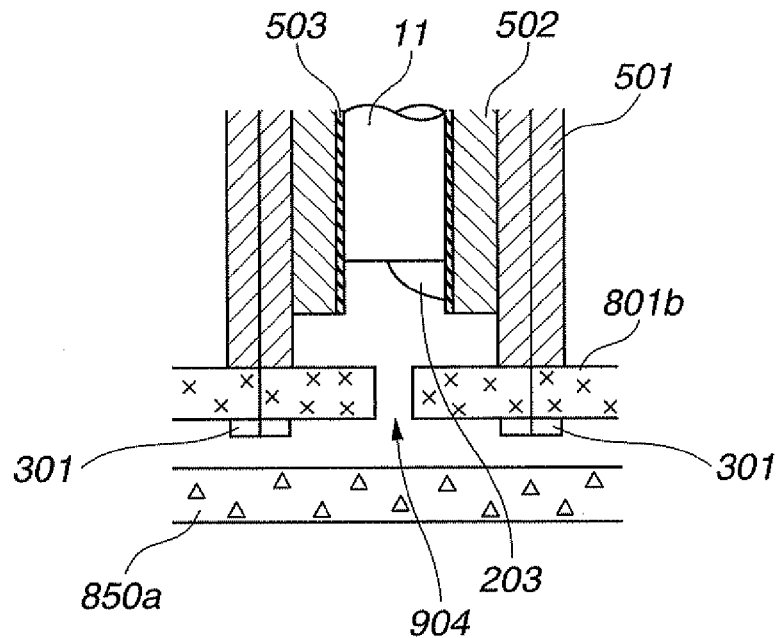

As a first opening formation step, in step S7, as shown in FIG. 22, the ultrasonic endoscope system 1 burns the luminal wall 801b of the jejunum 801 using an electric cautery 903 via the treatment instrument channel 11a of the ultrasonic endoscope 2 and, as shown in FIG. 23, forms a first opening 904 in the luminal wall 801a.

Figure 24:
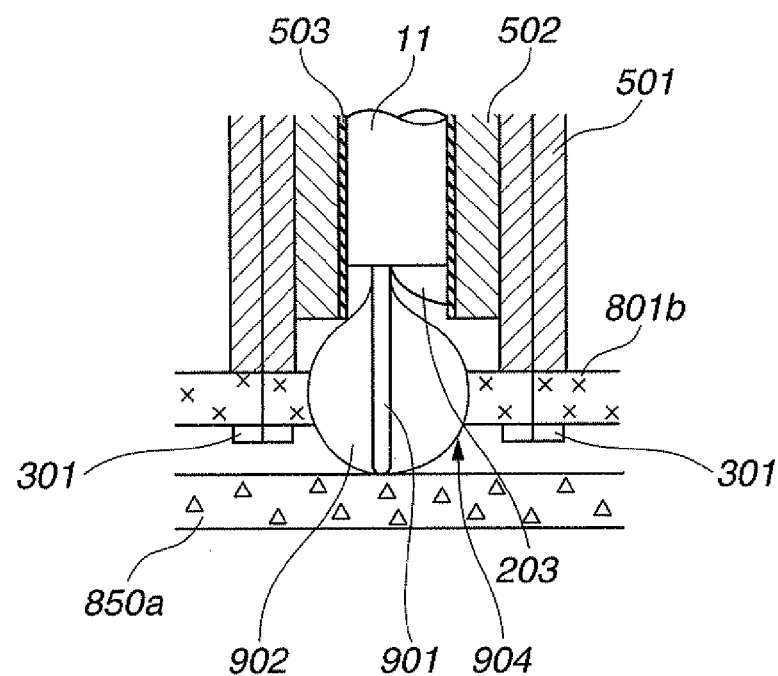
Figure 25:
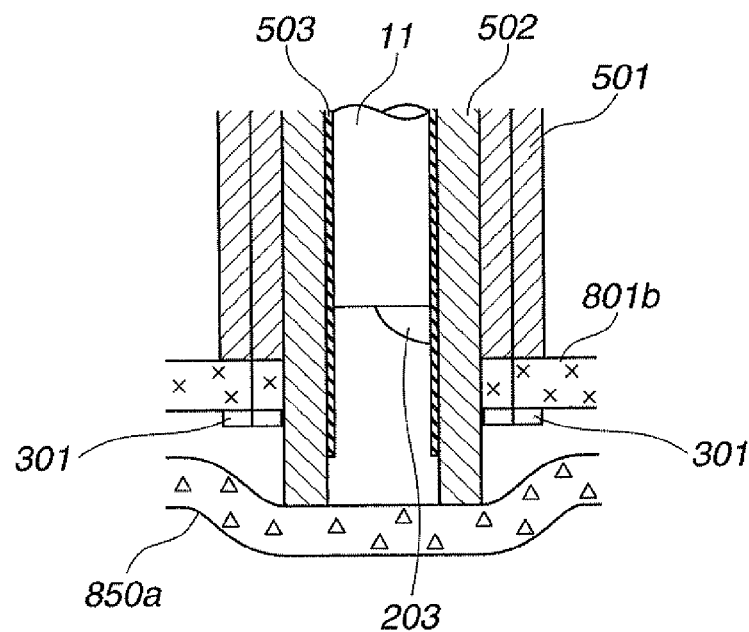

Next, as a separated area entering step, in step S8, as shown in FIG. 24, the ultrasonic endoscope system 1 inserts the distal end of the balloon treatment instrument 901 into the first opening 904 from the distal end opening 202 of the treatment instrument channel 11a. The ultrasonic endoscope system 1 inflates the balloon 902 at the distal end of the balloon treatment instrument 901 to expand the first opening 904. Subsequently, as shown in FIG. 25, the ultrasonic endoscope system 1 causes the cylindrical member 502 in the middle layer of the multi-lumen tube 500, in which the insertion portion 11 is inserted, to enter between the luminal wall 801b of the jejunum 801 and the luminal wall 850a of the remaining stomach 850 via the expanded first opening 904.

Figure 26:
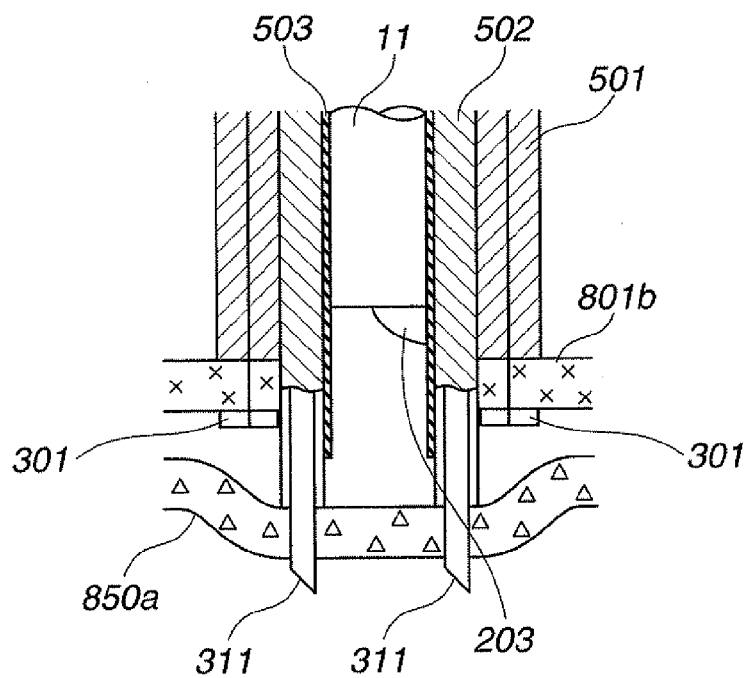
Figure 27:
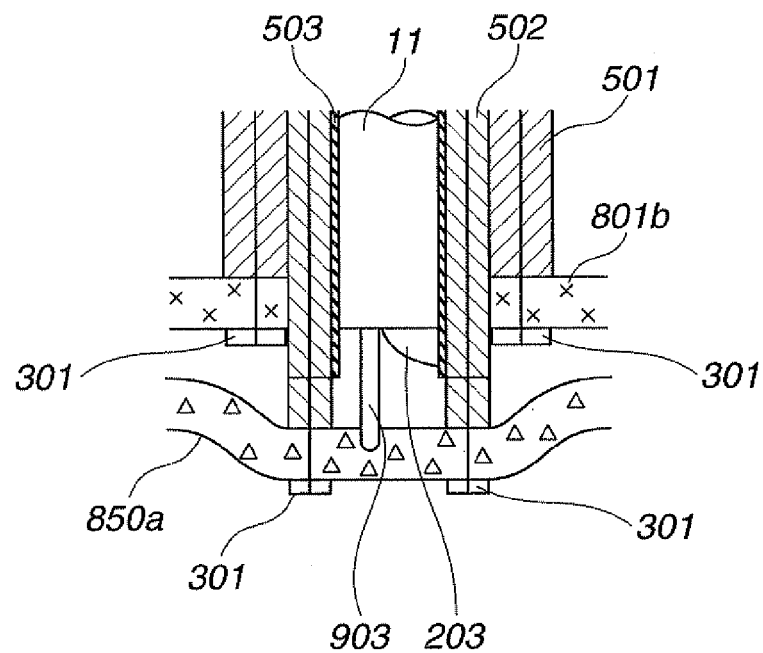

As a second opening forming step, in step 59, as shown in FIG. 26, the ultrasonic endoscope system 1 brings a distal end of the cylindrical member 502 in the intermediate layer of the multi-lumen tube 500 into contact with an outer wall of the luminal wall 850a of the remaining stomach 850 and inserts the needle-like member 311 of the T-bar injection portion 310 into the channel 510 of the cylindrical member 502 in the intermediate layer of the multi-lumen tube 500. The ultrasonic endoscope system 1 protrudes the distal end of the needle-like member 311 from the channel 510 and punctures the distal end into the inside of the luminal wall 850a of the remaining stomach 850 and locates the distal end bar member 301 of the T-bar portion 300 in the inside of the luminal wall 850a of the remaining stomach 850 from the distal end of the needle-like member 311. Subsequently, as shown in FIG. 27, the ultrasonic endoscope system 1 pulls the thread-like member 302 of the T-bar portion 300 toward the proximal end side of the insertion portion 11 to hold the distal end of the cylindrical member 502 in the intermediate layer of the multi-lumen tube 500 in a state in which the distal end is in contact with the outer wall of the luminal wall 850a of the remaining stomach 850. Consequently, a position of the distal end of the insertion portion 11 is held at a position where the second opening is formed.

Next, as a second opening forming step, as in the first opening forming step (step S7), in step S10, as shown in FIG. 27, the ultrasonic endoscope system 1 burns the luminal wall 850a of the remaining stomach 850 with the electric cautery 903 via the treatment instrument channel 11a of the ultrasonic endoscope 2 to form a second opening.

Figure 28:
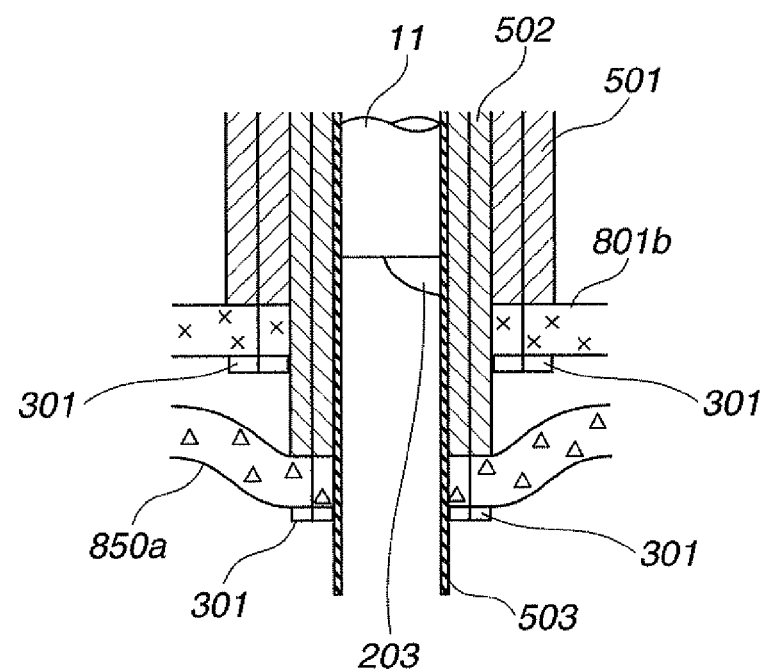

As an object organ entering step, in step S11, not shown in the figure, the ultrasonic endoscope system 1 inserts the distal end of the balloon treatment instrument 901 into the second opening from the distal end opening 202 of the treatment instrument channel 11a and inflates the balloon 902 at the distal end of the balloon treatment instrument 901 to expand the second opening. As shown in FIG. 28, the ultrasonic endoscope system 1 causes the cylindrical member 503 in the innermost layer of the multi-lumen tube 500, in which the insertion portion 11 is inserted, to enter into the inside of the luminal wall 850a of the remaining stomach 850, i.e., into the remaining stomach 850 via the expanded second opening.

Thereafter, as an observation treatment step, in step S12, the ultrasonic endoscope system 1 inserts the insertion portion 11 into the duodenum 802 from the remaining stomach 850 via the cylindrical member 503 in the innermost layer of the multi-lumen tube 500. In step S13, the ultrasonic endoscope system 1 performs optical and ultrasonic observation of the duodenum 802 and a region (the pancreatic duct, the biliary, etc.) connected or adjacent to the duodenum 802 and performs necessary endoscopic treatment.

In the present embodiment, in the observation treatment step, it is also possible to replace the endoscope in the multi-lumen tube 500 with another endoscope to perform observation and treatment.

As a first endoscope removing step, in step S14, the ultrasonic endoscope system 1 removes the insertion portion 11 from the duodenum 802 and the remaining stomach 850 and locates the distal end of the insertion portion 11 at a position between the luminal wall 801b of the jejunum 801 and the luminal wall 850a of the remaining stomach 850 separated from each other.

In a state in which the insertion portion 11 is removed to the position, as a first stitching step, in step S15, the ultrasonic endoscope system 1 stitches the second opening using a stitching treatment instrument (not shown) via the distal end opening 202 of the treatment instrument channel 11a.

Next, as a second endoscope removing step, in step S16, the ultrasonic endoscope system 1 removes the insertion portion 11 from the position between the luminal wall 801b of the jejunum 801 and the luminal wall 850a of the remaining stomach 850 into the jejunum 801 and locates the distal end of the insertion portion 11 in the jejunum 801.

In a state in which the insertion portion 11 is removed to the position, as a second stitching step, in step S17, the ultrasonic endoscope system 1 stitches the first opening 904 using the stitching treatment instrument (not shown) from the distal end opening 202 of the treatment instrument channel 11a.

Finally, in step S18, the ultrasonic endoscope system 1 removes the insertion portion 11 of the ultrasonic endoscope 2 from the body cavity and finishes the intraluminal endoscope inserting method according to the present embodiment.

With the intraluminal endoscope inserting method performed by using the ultrasonic endoscope system 1 according to the present embodiment described above, even in luminal organs of a patient (e.g., a patient to whom an inter-digestive tract bypass surgery for surgical treatment as anti-obesity measures is applied), of which the body cavity has the luminal organs irregularly connected to one another therein, it is possible to set an insertion path of the endoscope substantially identical with an insertion path of the ordinary endoscope test. Therefore, it is possible to use the ordinary endoscope without using a special endoscope (e.g., a W balloon endoscope) and make it easy to perform an endoscope inserting method.

As an example in which luminal organs are irregularly connected to one another in a body cavity, the luminal organs to which the inter-digestive tract bypass surgery for surgical treatment as anti-obesity measures are explained above. However, the present invention is not limited thereto. It is also possible to apply the present invention to luminal organs to which the inter-digestive tract bypass surgery because a part of the stomach is removed because of stomach cancer or the like.

In the example explained in the present embodiment, the intraluminal endoscope inserting method is performed between the jejunum and the remaining stomach. However, it is also possible to apply the intraluminal endoscope inserting method according to the present invention for among the other luminal organs irregularly connected to one another. It is also possible to apply the present invention when luminal organs are irregularly connected to one another inherently.

In the present embodiment, the first opening and the second opening are stitched in the first stitching step (step S15) and the second stitching step (step S17). It is also possible that the first stitching step (step S15) and the second stitching step (step S17) are omitted, and the first opening and the second opening are left opened.

In the case, by maintaining the opened state of the first opening and the second opening, in the intraluminal endoscope inserting method in the next time, it is possible to omit the first opening forming step (step S7) and the second opening forming step (step S10). Therefore, it is possible not only to further reduce burdens on the patient but also to carry out the intraluminal endoscope inserting method simply by optically finding out the first opening and the second opening. It is also possible to omit the step of specifying formation positions of the first opening and the second opening under the observation performed by using ultrasound and more easily carry out the intraluminal endoscope inserting method.

Modification

Figure 29:
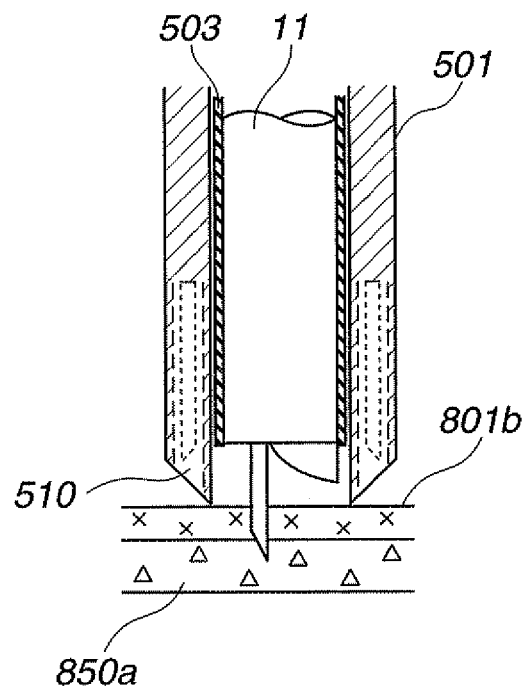
FIGS. 29 to 34 relate to a modification of the first embodiment of the present invention.

A modification of the present embodiment is explained below. In the first embodiment, the multi-lumen tube has the three-layer structure. However, as shown in FIG. 29, the multi-lumen tube 500 of the modification is formed in a two-layer structure formed of two layers of cylindrical members. The plural channels 510 for inserting various plural treatment instruments are formed in the inside of the wall of the cylindrical member 501 in the outer layer. The insertion portion 11 of the ultrasonic endoscope 2 is inserted into the cylindrical member 503 in the inner layer of the multi-lumen tube 500. The cylindrical members 501 and 503 are capable of holding the members inserted therein (the cylindrical member 503 in the cylindrical member 501 and the insertion portion 11 of the ultrasonic endoscope 2 in the cylindrical member 503) to freely move forward and backward.

In the modification physiological saline are injected into a space between both the walls (the luminal wall 801b and the luminal wall 850a) via a puncture needle 1500 to separate both the walls (see FIG. 29).

An intraluminal endoscope inserting method according to the modification is substantially the same as that according to the first embodiment. The modification is different from the first embodiment in the first position holding step in step S6 after the endoscope inserting step in steps S1 and S2, the adjacent organ confirming step in step S3, the safe area confirming step in step S4, and the separated area forming step in step S5 explained with reference to FIGS. 14 and 15.

Figure 30:
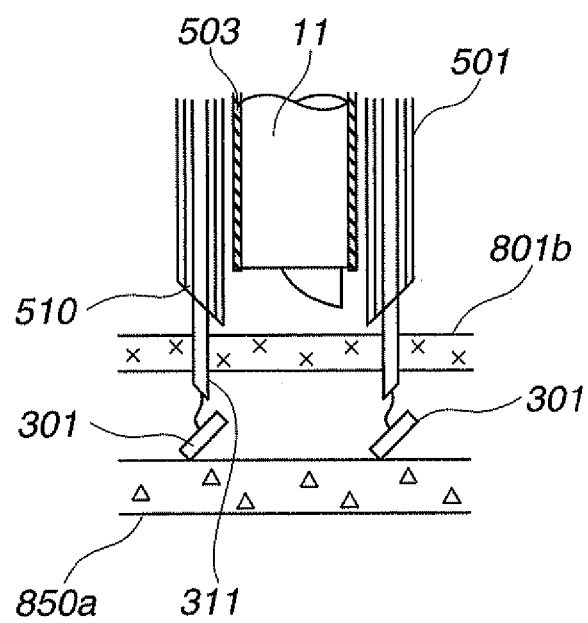

In the first position holding step in step S6 according to the modification, as shown in FIG. 30, the ultrasonic endoscope system 1 inserts the needle-like member 311 of the T-bar injection portion 310 into the channel 510 of the cylindrical member 501 in the outer circumference of the multi-lumen tube 500. The ultrasonic endoscope system 1 protrudes the distal end of the needle-like member 311 from the channel 510, punctures the distal end between the luminal wall 801b of the jejunum 801 and the luminal wall 850a of the remaining stomach 850 separated from each other by the injection of the physiological saline, and locates the distal end bar member 301 of the T-bar portion 300 between the luminal wall 801b of the jejunum 801 and the luminal wall 850a of the remaining stomach 850 from the distal end of the needle-like member 311. Subsequently, the ultrasonic endoscope system 1 pulls the thread-like member 302 of the T-bar portion 300 toward the proximal end side of the insertion portion 11 to hold the distal end of the cylindrical member 501 in the outer circumference of the multi-lumen tube 500 in a state in which the distal end is in contact with the inner wall of the luminal wall 801b of the jejunum 801. Consequently, a position of the distal end of the insertion portion 11 is held at a position where the first opening is formed.

Figure 31:
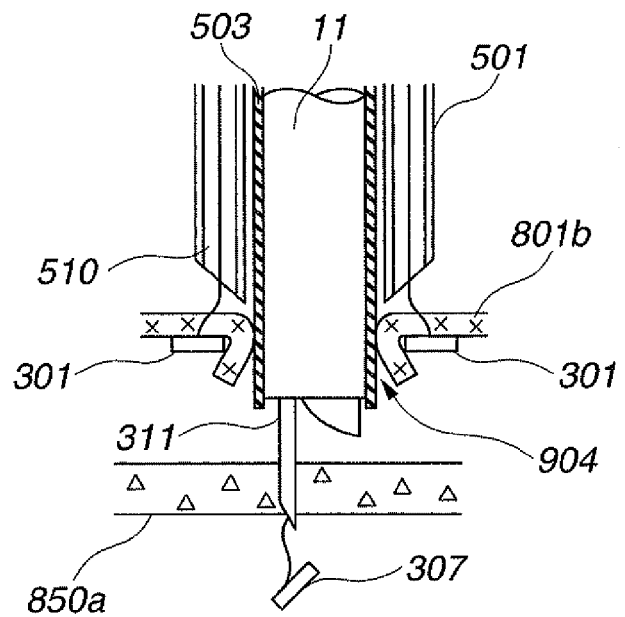

After the formation of the first opening in the first opening forming step in step S7, in the separated area entering step in step S8 according to the modification, as shown in FIG. 31, the ultrasonic endoscope system 1 inserts the cylindrical member 503 in the inner layer into the first opening 904 and causes the cylindrical member 503 in the inner layer of the multi-lumen tube 500, in which the insertion portion 11 is inserted, to enter into a space between the luminal wall 801b of the jejunum 801 and the luminal wall 850a of the remaining stomach 850 separated from each other while expanding the first opening 904.

Figure 32:
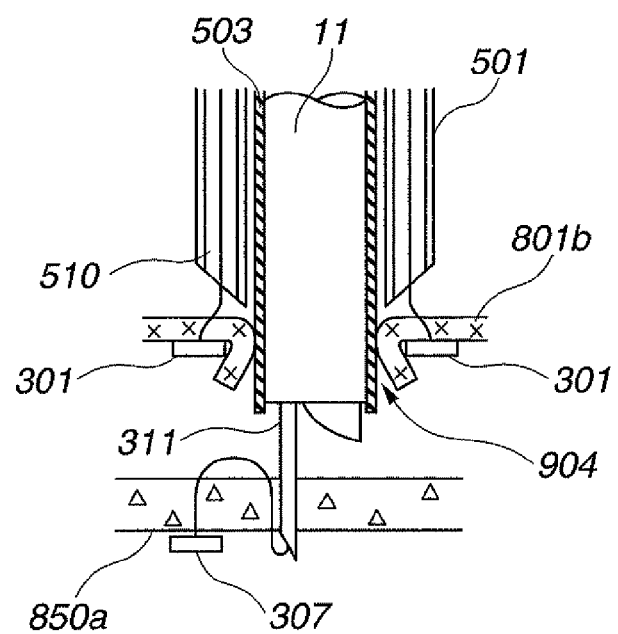
Figure 33:
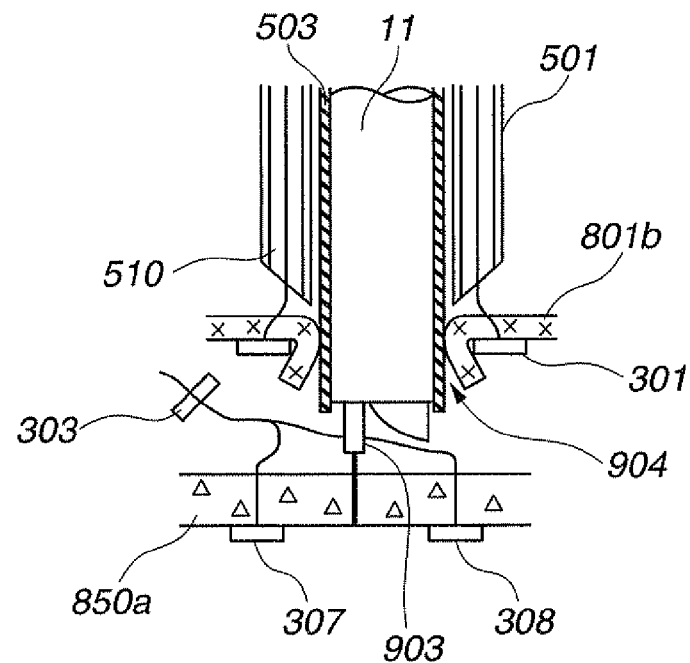

Thereafter, in the modification, in the second opening forming step in step S9, as shown in FIGS. 31 to 33, the ultrasonic endoscope system 1 inserts the needle-like member 311 of the T-bar injection portion 310 into the treatment instrument channel 11a of the insertion portion 11 inserted into the cylindrical member 503 in the inner layer of the multi-lumen tube 500. The ultrasonic endoscope system 1 protrudes the distal end of the needle-like member 311 from the channel 510, punctures the distal end in the luminal wall 850a of the remaining stomach 850, and locates the first distal end bar member 307 of the forked T-bar portion 309 (see FIG. 5) from the distal end of the needle-like member 311. In the same manner, the ultrasonic endoscope system 1 locates the second distal end bar member 308 of the forked T-bar portion 309 in the luminal wall 850a of the remaining stomach 850 from the distal end of the needle-like member 311. The ultrasonic endoscope system 1 pulls the first thread-like member 305 and the second thread-like member 306 of the forked T-bar portion 309 to the center bar member 303. Consequently, a position of the distal end of the insertion portion 11 is held at a position where the second opening is formed.

Figure 34:
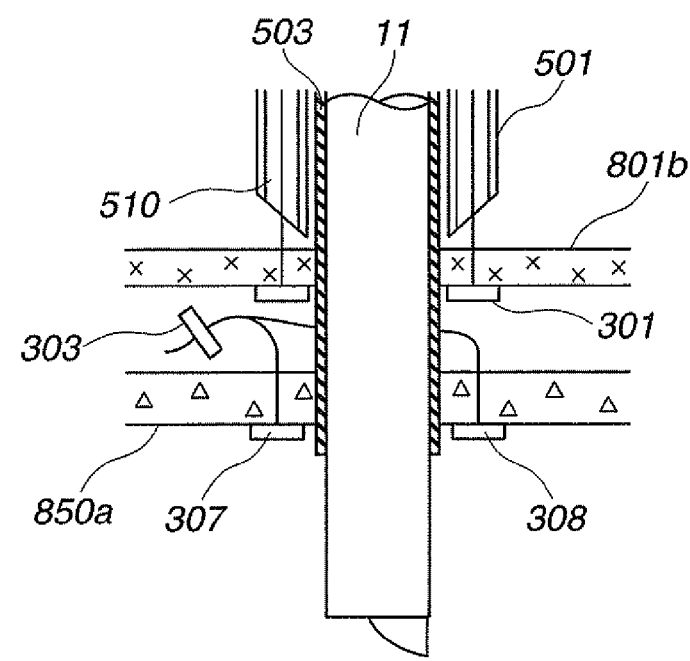

After the formation of the second opening in the second opening forming step in step S10, as shown in FIG. 34, in the object organ entering step in step S11, the ultrasonic endoscope system 1 inserts the cylindrical member 503 in the inner layer into the first opening 904 and causes the cylindrical member 503 in the inner layer of the multi-lumen tube 500, in which the insertion portion 11 is inserted, to enter into the luminal wall 850a of the remaining stomach 850, i.e., into the remaining stomach 850 while expanding the first opening 904.

Processing steps thereafter are the same as those according to the first embodiment.

In the way, in the modification, actions and effects same as those in the first embodiment can be obtained.

Figure 35:
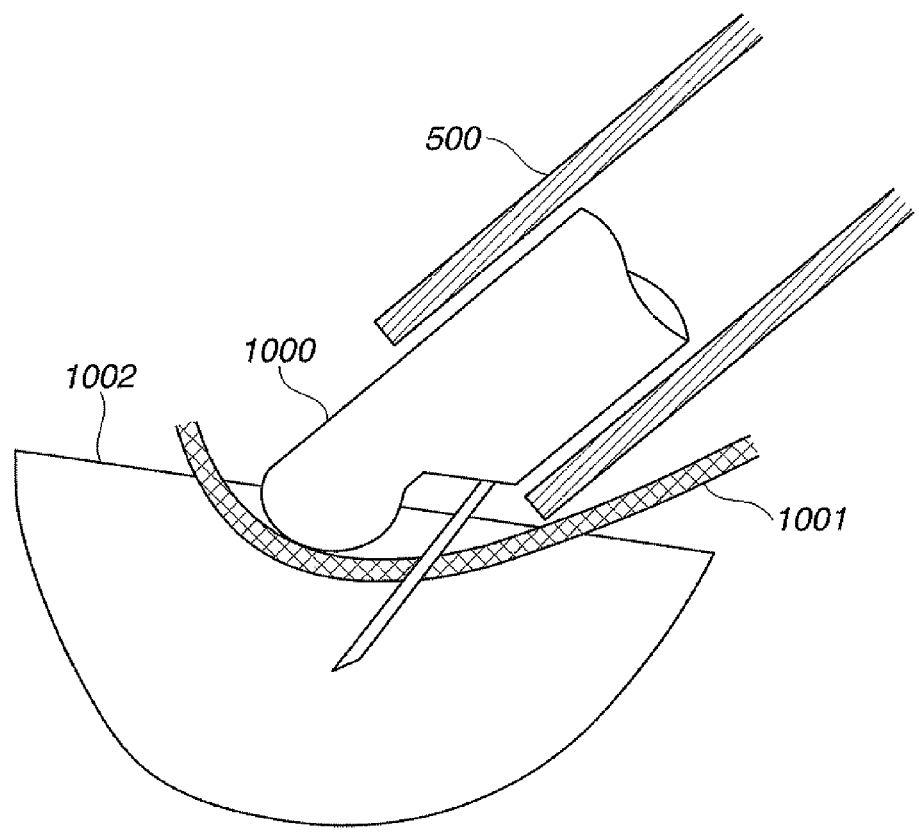
FIG. 35 is a diagram showing a modification of the ultrasonic endoscope according to the first embodiment of the present invention.

In the first embodiment and the modification thereof, the ultrasonic endoscope 2 is the direct-vision convex-type ultrasonic endoscope. However, even when a skew-view convex-type ultrasonic endoscope 1000, which is a skew-view ultrasonic endoscope in which, for example, an optical system is skew-view rather than direct-view shown in FIG. 35, is used, it is possible to carry out the intraluminal endoscope inserting method in the same manner by inserting an insertion portion of the skew-view convex-type ultrasonic endoscope 1000 through the multi-lumen tube 500, transmitting and receiving ultrasound 1002 to and from a luminal wall 1001, and performing optical observation and ultrasonic observation. Reference numeral 1002 in FIG. 35 is a schematic illustration of an ultrasonic scanning surface.

Figure 36:
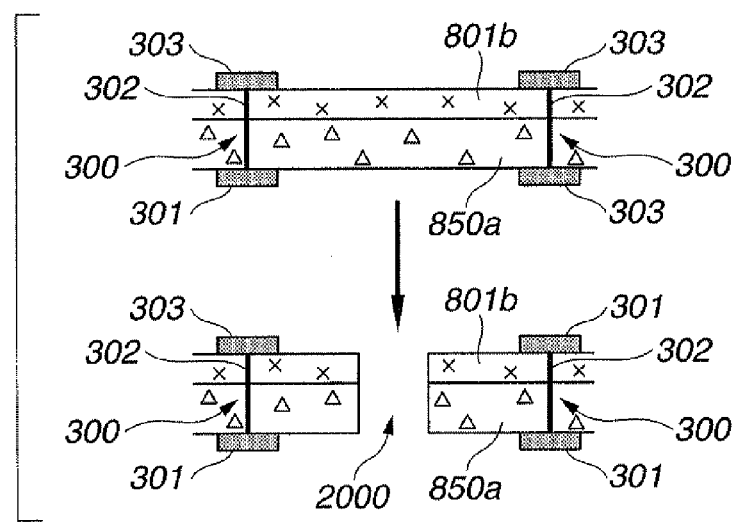
FIG. 36 is a diagram for explaining a modification of an entering step into an object organ step of the ultrasonic endoscope according to the first embodiment of the present invention.

As shown in FIG. 36, it is also possible that in both the walls (the luminal wall 801b and the luminal wall 850a), plural T-bar portions 300 are temporarily retained under the ultrasonic guide, a region between the T-bar portions 300 is dissectioned to form an opening 2000, and the endoscope is inserted through a hole of the opening 2000. The hole may be closed by using another forked T-bar portion 309 or may be left as it is.

It is also possible that the T-bar portions 300 are retained, and an opening may be endoscopically formed later when both the walls (the luminal wall 801b and the luminal wall 850a) adhere to each other.

In the present invention, it is evident that different embodiments can be carried out on the basis of the present invention without departing from the spirit and the scope of the present invention. The present invention is not limited by specific embodiments thereof except that the present invention is limited by the appended claims.

What is claimed is:

1. An intraluminal endoscope inserting method for inserting an endoscope into a luminal organ of a patient having a stomach divided into a stomach esophagus side and a stomach duodenum side and a small intestine divided into a duodenum side and a large intestine side, the stomach duodenum side being connected to the small intestine at a jejunum, the stomach esophagus side being connected to the small intestine at a position proximal to the jejunum and the small intestine on the duodenum side connected to a portion of the small intestine on the large intestine side, the intraluminal endoscope inserting method comprising:

an endoscope inserting step of inserting an insertion portion of the endoscope including an ultrasonic observation unit into a first object luminal organ, the first object luminal organ being the stomach esophagus side, through a natural opening of the patient;

an adjacent organ confirming step of transmitting and receiving ultrasound inside the first object luminal organ and confirming a second object luminal organ, the second object luminal organ being the stomach duodenum side, adjacent to the first object luminal organ;
a first opening forming step of forming a first opening in a tube wall of the first object luminal organ after the adjacent organ confirming step;
a second opening forming step of forming a second opening in a tube wall of the second object luminal organ after the adjacent organ confirming step;
an object organ entering step of causing a distal end of the insertion portion of the endoscope to enter an internal area of the second object luminal organ from the second opening; and
an observing and treating step of observing and treating the second object luminal organ with the endoscope.

2. The intraluminal endoscope inserting method according to claim 1, further comprising:
a safe area confirming step of confirming, under observation of the endoscope, a safe area, which is an area in which there is no body cavity organs other than the first object luminal organ and the second luminal organ, in an inter-organ area between the first object luminal organ and the second object luminal organ, wherein
in the first opening forming step, the first opening is formed in the tube wall of the first object luminal organ in a vicinity of the safe area confirmed in the safe area confirming step, and
in the second opening forming step, in a state in which the distal end of the insertion portion of the endoscope is caused to enter a separated space, the second opening is formed in the tube wall of the second object luminal organ in the vicinity of the safe area confirmed in the safe area confirming step.

3. The intraluminal endoscope inserting method according to claim 2, wherein
the endoscope is an ultrasonic endoscope having, at the distal end thereof, an optical observation unit that optically observes an observation region and an ultrasonic observation unit that is capable of observing the observation region with ultrasound,
in the adjacent organ confirmation step and the safe area confirmation step, area confirmation is performed by ultrasonic observation of the ultrasonic observation unit.

4. The intraluminal endoscope inserting method according to claim 3, wherein the endoscope has an endoscope treatment instrument channel for inserting a treatment instrument.

5. The intraluminal endoscope inserting method according to claim 4, further comprising:
a separated area entering step of, after the first opening forming step, causing the distal end of the insertion portion of the endoscope to enter the separated area from the first opening; and
a separated area forming step of expanding at least the safe area of the inter-organ area and forming a separated area in which the first object luminal organ and the second object luminal organs are separated, wherein
in the separated area forming step, the separated area is formed by an expanding treatment instrument inserted through the endoscope treatment instrument channel.

6. The intraluminal endoscope inserting method according to claim 5, wherein
the expanding treatment instrument is a balloon treatment instrument inserted through the endoscope treatment instrument channel, and
in the separated area forming step, a distal end of the balloon treatment instrument is punctured from an inside of the tube wall of the first object luminal organ and protruded to an outside and a balloon of the balloon treatment instrument is expanded at the distal end of the balloon treatment instrument protruded to the outside of the first object luminal organ to separate the first object luminal organ and the second object luminal organ and form the separated area.

7. The intraluminal endoscope inserting method according to claim 5, wherein
the expanding treatment instrument is a fluid injection treatment instrument inserted through the endoscope treatment instrument channel, and
in the separated area forming step, a distal end of the fluid injection treatment instrument is punctured from an inside of the tube wall of the first object luminal organ and protruded to an outside and a fluid is injected into a space between the first object luminal organ and the second object luminal organ from the distal end of the fluid injection treatment instrument protruded to the outside of the first object luminal organ to separate the first object luminal organ and the second object luminal organ with the fluid and form the separated area.

8. The intraluminal endoscope inserting method according to claim 5, wherein, in the first opening forming step, the first opening is formed by an opening formation treatment instrument inserted through the endoscope treatment instrument channel.

9. The intraluminal endoscope inserting method according to claim 8, wherein, in the second opening forming step, the second opening is formed by the opening formation treatment instrument.

10. The intraluminal endoscope inserting method according to claim 9, wherein the insertion portion of the endoscope is inserted through the multi-lumen tube, which is formed of plural cylindrical members of laminated wall structure having channels for inserting a treatment tool therethrough, and inserted into the first object luminal organ via the multi-lumen tube in the endoscope inserting step.

11. The intraluminal endoscope inserting method according to claim 10, further comprising a first position holding step of holding, after the separated area forming step, a position of the distal end of the insertion portion of the endoscope at a position where the first opening is formed.

12. The intraluminal endoscope inserting method according to claim 11, wherein, in the first position holding step, the position of the distal end of the insertion portion of the endoscope is held at the position, where the first opening is formed, by a holding treatment instrument inserted through a channel of a first cylindrical member of the multi-lumen tube.

13. The intraluminal endoscope inserting method according to claim 12, further comprising a second position holding step of holding, after the separated area entering step, the position of the distal end of the insertion portion of the endoscope at a position where the second opening is formed.

14. The intraluminal endoscope inserting method according to claim 13, in the second position holding step, the position of the distal end of the insertion portion of the endoscope is held at the position, where the second opening is formed, by the holding treatment instrument inserted through a channel of a second cylindrical member of the multi-lumen tube.

15. The intraluminal endoscope inserting method according to claim 2, further comprising:
a first endoscope removing step of removing the endoscope from the first opening after the observing and treating step;
a first stitching step of stitching the first opening after the first endoscope removing step;

a second endoscope removing step of removing the endoscope from the second opening after the observing and treating step; and a second stitching step of stitching the second opening after the second endoscope removing step.

16. The intraluminal endoscope inserting method according to claim 3, further comprising:

a first endoscope removing step of removing the endoscope from the first opening after the observing and treating step;

a first stitching step of stitching the first opening after the first endoscope removing step;

a second endoscope removing step of removing the endoscope from the second opening after the observing and treating step; and a second stitching step of stitching the second opening after the second endoscope removing step.

17. The intraluminal endoscope inserting method according to claim 4, in the separated area forming step, with a balloon of a balloon treatment instrument inserted through the endoscope treatment instrument channel, the balloon is inflated between the first object luminal organ and the second object luminal organ to separate the object luminal organs and form the separated area.

18. The intraluminal endoscope inserting method according to claim 4, wherein, in the separated area forming step, a fluid is injected into a space between the first object luminal organ and the second object luminal organ by a fluid injection treatment instrument inserted through the endoscope treatment instrument channel to separate the object luminal organs and form the separated area.

19. The intraluminal endoscope inserting method according to claim 4, wherein the endoscope has a rising stand at a distal end opening of the endoscope treatment instrument channel.

20. An intraluminal endoscope inserting method for inserting an endoscope into a luminal organ of a patient having a stomach divided into a stomach esophagus side and a stomach duodenum side and a small intestine divided into a duodenum side and a large intestine side, the stomach duodenum side being connected to the small intestine at a jejunum, the stomach esophagus side being connected to the small intestine at a position proximal to the jejunum and the small intestine on the duodenum side connected to a portion of the small intestine on the large intestine side, the intraluminal endoscope inserting method comprising:

an endoscope inserting step of inserting an insertion portion of an endoscope including an ultrasonic observation unit into a first object luminal organ, the first object luminal organ being the stomach esophagus side, through a natural opening of the patient;

an adjacent organ confirming step of confirming, under ultrasonic observation of the endoscope, a second object luminal organ, the second object luminal organ being the stomach duodenum side, adjacent to an outer wall surface of the first object luminal organ;

a safe area confirming step of confirming, under observation of the endoscope, a safe area, which is an area in which there is no body cavity organs other than the first object luminal organ and the second luminal organ, in an inter-organ area between the first object luminal organ and the second object luminal organ;

a separated area forming step of expanding at least the safe area of the inter-organ area and forming a separated area in which the first object luminal organ and the second object luminal organs are separated;

a first opening forming step of forming a first opening in a tube wall of the first object luminal organ in the vicinity of the safe area confirmed in the safe area confirming step after the adjacent organ confirming step;

a separated area entering step of causing a distal end of the insertion portion of the endoscope to enter the separated area from the first opening;

a second opening forming step of, in a state in which the distal end of the insertion portion of the endoscope is caused to enter the separated space, a second opening in a tube wall of the second object luminal organ near the safe area confirmed in the safe area confirming step;

an object organ entering step of causing the distal end of the insertion portion of the endoscope to enter an internal area of the second object luminal organ from the second opening;

an observing and treating step of observing and treating the second object luminal organ with the endoscope;

a first endoscope removing step of removing the endoscope from the first opening;

a first stitching step of stitching the first opening after the first endoscope removing step;

a second endoscope removing step of removing the endoscope from the second opening after the observing and treating step; and a second stitching step of stitching the second opening after the second endoscope removing step.

* * * * *